US009623161B2

(12) United States Patent
Medvedev et al.

(10) Patent No.: US 9,623,161 B2
(45) Date of Patent: *Apr. 18, 2017

(54) BLOOD PUMP AND METHOD OF SUCTION DETECTION

(71) Applicant: TC1 LLC, Pleasanton, CA (US)

(72) Inventors: Alexander Medvedev, Ann Arbor, MI (US); J. Bradford Rainier, Chelsea, MI (US); Muhammad K. Sami, Ypsilanti, MI (US)

(73) Assignee: TC1 LLC, Pleasanton, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/834,757

(22) Filed: Aug. 25, 2015

(65) Prior Publication Data

US 2016/0058929 A1 Mar. 3, 2016

Related U.S. Application Data

(60) Provisional application No. 62/041,910, filed on Aug. 26, 2014.

(51) Int. Cl.
*A61N 1/362* (2006.01)
*A61M 1/10* (2006.01)
*A61M 1/12* (2006.01)

(52) U.S. Cl.
CPC ........... *A61M 1/1086* (2013.01); *A61M 1/101* (2013.01); *A61M 1/122* (2014.02); *A61M 2205/3334* (2013.01); *A61M 2205/50* (2013.01)

(58) Field of Classification Search
CPC .... A61M 1/10; A61M 1/1001; A61M 1/1005; A61M 1/1086
See application file for complete search history.

(56) References Cited

U.S. PATENT DOCUMENTS 1,093,868 A 4/1914 Leighty
2,684,035 A 7/1954 Kemp
(Continued)

FOREIGN PATENT DOCUMENTS

CN 1347585 A 5/2002
CN 1462344 A 12/2003
(Continued)

OTHER PUBLICATIONS

Asama, J., et al., "A Compact Highly Efficient and Low Hemolytic Centrifugal Blood Pump With a Magnetically Levitated Impeller", Artificial Organs, vol. 30, No. 3, Mar. 1, 2006 (Mar. 1, 2006), pp. 160-167.
(Continued)

*Primary Examiner* — Robert N Wieland
(74) *Attorney, Agent, or Firm* — Kilpatrick Townsend & Stockton LLP

(57) ABSTRACT

A system and method for detecting and mitigating a suction condition are disclosed. The method may include estimating a flow waveform of the pump, identifying pulses in the flow waveform, determining a negative flow based on a valid identification of a pulse, and evaluating a characteristic of the pulse for an existence of a suction condition. In various embodiments, a suction marker is located based on a minimum in a diastolic phase, and the suction marker location is used to identify a probability of a suction condition. A speed of the pump may be adjusted to mitigate the suction condition. A system and method for estimating flow is further disclosed. The method may include interpolating data sets defining pump power to flow for various pump speed values.

14 Claims, 12 Drawing Sheets

(56) References Cited

U.S. PATENT DOCUMENTS

| | | | |
|---|---|---|---|
| 3,023,334 | A | 2/1962 | Burr et al. |
| 3,510,229 | A | 5/1970 | Smith |
| 3,620,638 | A | 11/1971 | Kaye et al. |
| 3,870,382 | A | 3/1975 | Reinhoudt |
| 3,932,069 | A | 1/1976 | Giardini et al. |
| 3,960,468 | A | 6/1976 | Boorse et al. |
| 4,149,535 | A | 4/1979 | Voider |
| 4,382,199 | A | 5/1983 | Isaacson |
| 4,392,836 | A | 7/1983 | Sugawara |
| 4,434,389 | A | 2/1984 | Langley et al. |
| 4,507,048 | A | 3/1985 | Belenger et al. |
| 4,528,485 | A | 7/1985 | Boyd, Jr. |
| 4,540,402 | A | 9/1985 | Aigner |
| 4,549,860 | A | 10/1985 | Yakich |
| 4,645,961 | A | 2/1987 | Maisky |
| 4,686,982 | A | 8/1987 | Nash |
| 4,688,998 | A | 8/1987 | Olsen et al. |
| 4,753,221 | A | 6/1988 | Kensey et al. |
| 4,769,006 | A | 9/1988 | Papatonakos |
| 4,779,614 | A | 10/1988 | Moise |
| 4,790,843 | A | 12/1988 | Carpentier et al. |
| 4,806,080 | A | 2/1989 | Mizobuchi et al. |
| 4,817,586 | A | 4/1989 | Wampler |
| 4,846,152 | A | 7/1989 | Wampler et al. |
| 4,857,781 | A | 8/1989 | Shih |
| 4,888,011 | A | 12/1989 | Kung et al. |
| 4,895,557 | A | 1/1990 | Moise et al. |
| 4,900,227 | A | 2/1990 | Trouplin |
| 4,902,272 | A | 2/1990 | Milder et al. |
| 4,906,229 | A | 3/1990 | Wampler |
| 4,908,012 | A | 3/1990 | Moise et al. |
| 4,919,647 | A | 4/1990 | Nash |
| 4,930,997 | A | 6/1990 | Bennett |
| 4,944,722 | A | 7/1990 | Carriker et al. |
| 4,957,504 | A | 9/1990 | Chardack |
| 4,964,864 | A | 10/1990 | Summers et al. |
| 4,969,865 | A | 11/1990 | Hwang et al. |
| 4,985,014 | A | 1/1991 | Orejola |
| 4,995,857 | A | 2/1991 | Arnold |
| 5,021,048 | A | 6/1991 | Buckholtz |
| 5,078,741 | A | 1/1992 | Bramm et al. |
| 5,092,844 | A | 3/1992 | Schwartz et al. |
| 5,092,879 | A | 3/1992 | Jarvik |
| 5,100,374 | A | 3/1992 | Kageyama et al. |
| 5,106,263 | A | 4/1992 | Irie |
| 5,106,273 | A | 4/1992 | Lemarquand et al. |
| 5,106,372 | A | 4/1992 | Ranford |
| 5,112,202 | A | 5/1992 | Ozaki et al. |
| 5,112,349 | A | 5/1992 | Summers et al. |
| 5,129,883 | A | 7/1992 | Black |
| 5,145,333 | A | 9/1992 | Smith |
| 5,147,186 | A | 9/1992 | Buckholtz |
| 5,190,528 | A | 3/1993 | Fonger et al. |
| 5,201,679 | A | 4/1993 | Velte et al. |
| 5,211,546 | A | 5/1993 | Isaacson et al. |
| 5,229,693 | A | 7/1993 | Futami et al. |
| 5,275,580 | A | 1/1994 | Yamazaki |
| 5,290,227 | A | 3/1994 | Pasque |
| 5,290,236 | A | 3/1994 | Mathewson |
| 5,300,112 | A | 4/1994 | Barr |
| 5,306,295 | A | 4/1994 | Kolff et al. |
| 5,312,341 | A | 5/1994 | Turi |
| 5,313,128 | A | 5/1994 | Robinson et al. |
| 5,332,374 | A | 7/1994 | Kricker et al. |
| 5,346,458 | A | 9/1994 | Afield |
| 5,350,283 | A | 9/1994 | Nakazeki et al. |
| 5,354,331 | A | 10/1994 | Schachar |
| 5,360,445 | A | 11/1994 | Goldowsky |
| 5,370,509 | A | 12/1994 | Golding et al. |
| 5,376,114 | A | 12/1994 | Jarvik |
| 5,385,581 | A | 1/1995 | Bramm et al. |
| 5,405,383 | A | 4/1995 | Barr |
| 5,449,342 | A | 9/1995 | Hirose et al. |
| 5,478,222 | A | 12/1995 | Heidelberg et al. |
| 5,504,978 | A | 4/1996 | Meyer, III |
| 5,507,629 | A | 4/1996 | Jarvik |
| 5,519,270 | A | 5/1996 | Yamada et al. |
| 5,533,957 | A | 7/1996 | Aldea |
| 5,569,111 | A | 10/1996 | Cho et al. |
| 5,575,630 | A | 11/1996 | Nakazawa et al. |
| 5,588,812 | A | 12/1996 | Taylor et al. |
| 5,595,762 | A | 1/1997 | Derrieu et al. |
| 5,611,679 | A | 3/1997 | Ghosh et al. |
| 5,613,935 | A | 3/1997 | Jarvik |
| 5,630,836 | A | 5/1997 | Prem et al. |
| 5,643,226 | A | 7/1997 | Cosgrove et al. |
| 5,678,306 | A | 10/1997 | Bozeman, Jr. et al. |
| 5,692,882 | A | 12/1997 | Bozeman, Jr. et al. |
| 5,695,471 | A | 12/1997 | Wampler |
| 5,708,346 | A | 1/1998 | Schob |
| 5,725,357 | A | 3/1998 | Nakazeki et al. |
| 5,738,649 | A | 4/1998 | Macoviak |
| 5,746,575 | A | 5/1998 | Westphal et al. |
| 5,746,709 | A | 5/1998 | Rom et al. |
| 5,749,855 | A | 5/1998 | Reitan |
| 5,755,784 | A | 5/1998 | Jarvik |
| 5,776,111 | A | 7/1998 | Tesio |
| 5,795,074 | A | 8/1998 | Rahman et al. |
| 5,800,559 | A | 9/1998 | Higham et al. |
| 5,807,311 | A | 9/1998 | Palestrant |
| 5,814,011 | A | 9/1998 | Corace |
| 5,824,069 | A | 10/1998 | Lemole |
| 5,843,129 | A | 12/1998 | Larson et al. |
| 5,851,174 | A | 12/1998 | Jarvik et al. |
| 5,853,394 | A | 12/1998 | Tolkoff et al. |
| 5,868,702 | A | 2/1999 | Stevens et al. |
| 5,868,703 | A | 2/1999 | Bertolero et al. |
| 5,888,242 | A | 3/1999 | Antaki et al. |
| 5,890,883 | A | 4/1999 | Golding et al. |
| 5,911,685 | A | 6/1999 | Siess et al. |
| 5,917,295 | A | 6/1999 | Mongeau |
| 5,917,297 | A | 6/1999 | Gerster et al. |
| 5,921,913 | A | 7/1999 | Siess |
| 5,924,848 | A | 7/1999 | Izraelev |
| 5,924,975 | A | 7/1999 | Goldowsky |
| 5,928,131 | A | 7/1999 | Prem |
| 5,938,412 | A | 8/1999 | Izraelev |
| 5,941,813 | A | 8/1999 | Sievers et al. |
| 5,947,703 | A | 9/1999 | Nojiri et al. |
| 5,951,263 | A | 9/1999 | Taylor et al. |
| 5,964,694 | A | 10/1999 | Siess et al. |
| 6,004,269 | A | 12/1999 | Crowley et al. |
| 6,007,479 | A | 12/1999 | Rottenberg et al. |
| 6,030,188 | A | 2/2000 | Nojiri et al. |
| 6,042,347 | A | 3/2000 | Scholl et al. |
| 6,053,705 | A | 4/2000 | Schob et al. |
| 6,058,593 | A | 5/2000 | Siess |
| 6,066,086 | A | 5/2000 | Antaki et al. |
| 6,071,093 | A | 6/2000 | Hart |
| 6,074,180 | A | 6/2000 | Khanwilkar et al. |
| 6,080,133 | A | 6/2000 | Wampler |
| 6,082,900 | A | 7/2000 | Takeuchi et al. |
| 6,083,260 | A | 7/2000 | Aboul-Hosn et al. |
| 6,086,527 | A | 7/2000 | Talpade |
| 6,100,618 | A | 8/2000 | Schoeb et al. |
| 6,123,659 | A | 9/2000 | leBlanc et al. |
| 6,123,726 | A | 9/2000 | Mori et al. |
| 6,139,487 | A | 10/2000 | Siess |
| 6,142,752 | A | 11/2000 | Akamatsu et al. |
| 6,143,025 | A | 11/2000 | Stobie et al. |
| 6,146,325 | A | 11/2000 | Lewis et al. |
| 6,149,683 | A | 11/2000 | Lancisi et al. |
| 6,158,984 | A | 12/2000 | Cao et al. |
| 6,171,078 | B1 | 1/2001 | Schob |
| 6,176,822 | B1 | 1/2001 | Nix et al. |
| 6,176,848 | B1 | 1/2001 | Rau et al. |
| 6,179,773 | B1 | 1/2001 | Prem et al. |
| 6,190,304 | B1 | 2/2001 | Downey et al. |
| 6,200,260 | B1 | 3/2001 | Bolling |
| 6,206,659 | B1 | 3/2001 | Izraelev |
| 6,222,290 | B1 | 4/2001 | Schob et al. |
| 6,227,797 | B1 | 5/2001 | Watterson et al. |
| 6,227,820 | B1 | 5/2001 | Jarvik |
| 6,234,772 | B1 | 5/2001 | Wampler et al. |

(56) References Cited

U.S. PATENT DOCUMENTS

| | | |
|---|---|---|
| 6,234,998 B1 | 5/2001 | Wampler |
| 6,245,007 B1 | 6/2001 | Bedingham et al. |
| 6,247,892 B1 | 6/2001 | Kazatchkov et al. |
| 6,249,067 B1 | 6/2001 | Schob et al. |
| 6,254,359 B1 | 7/2001 | Aber |
| 6,264,635 B1 | 7/2001 | Wampler et al. |
| 6,268,675 B1 | 7/2001 | Amrhein |
| 6,276,831 B1 | 8/2001 | Takahashi et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,320,731 B1 | 11/2001 | Eeaves et al. |
| 6,351,048 B1 | 2/2002 | Schob et al. |
| 6,355,998 B1 | 3/2002 | Schob et al. |
| 6,365,996 B2 | 4/2002 | Schob |
| 6,375,607 B1 | 4/2002 | Prem |
| 6,387,037 B1 | 5/2002 | Bolling et al. |
| 6,394,769 B1 | 5/2002 | Bearnson et al. |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |
| 6,458,163 B1 | 10/2002 | Slemker et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,522,093 B1 | 2/2003 | Hsu et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,575,717 B2 | 6/2003 | Ozaki et al. |
| 6,589,030 B2 | 7/2003 | Ozaki |
| 6,595,762 B2 | 7/2003 | Khanwilkar et al. |
| 6,605,032 B2 | 8/2003 | Benkowski et al. |
| 6,609,883 B2 | 8/2003 | Woodard et al. |
| 6,610,004 B2 | 8/2003 | Viole et al. |
| 6,623,420 B2 | 9/2003 | Reich et al. |
| 6,632,169 B2 | 10/2003 | Korakianitis |
| 6,641,378 B2 | 11/2003 | Davis et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,157 B2 | 4/2004 | Goldowsky |
| 6,716,189 B1 | 4/2004 | Jarvik et al. |
| 6,732,501 B2 | 5/2004 | Yu et al. |
| 6,749,598 B1 | 6/2004 | Keren et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,846,168 B2 | 1/2005 | Davis et al. |
| 6,860,713 B2 | 3/2005 | Hoover |
| 6,884,210 B2 | 4/2005 | Nose et al. |
| 6,926,662 B1 | 8/2005 | Aboul-Hosn et al. |
| 6,935,344 B1 | 8/2005 | Aboul-Hosn et al. |
| 6,942,672 B2 | 9/2005 | Heilman et al. |
| 6,949,066 B2 | 9/2005 | Beamson et al. |
| 6,966,748 B2 | 11/2005 | Woodard et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,027,875 B2 | 4/2006 | Siess et al. |
| 7,048,681 B2 | 5/2006 | Tsubouchi et al. |
| 7,090,401 B2 | 8/2006 | Rahman et al. |
| 7,112,903 B1 | 9/2006 | Schob |
| 7,122,019 B1 | 10/2006 | Kesten et al. |
| 7,128,538 B2 | 10/2006 | Tsubouchi et al. |
| 7,156,802 B2 | 1/2007 | Woodard et al. |
| 7,160,243 B2 | 1/2007 | Medvedev |
| 7,172,551 B2 | 2/2007 | Leasure |
| 7,175,588 B2 | 2/2007 | Morello |
| 7,202,582 B2 | 4/2007 | Eckert et al. |
| 7,241,257 B1 | 7/2007 | Ainsworth et al. |
| 7,284,956 B2 | 10/2007 | Nose et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,393,181 B2 | 7/2008 | McBride et al. |
| 7,431,688 B2 | 10/2008 | Wampler et al. |
| 7,462,019 B1 | 12/2008 | Allarie et al. |
| 7,467,930 B2 | 12/2008 | Ozaki et al. |
| 7,470,246 B2 | 12/2008 | Mori et al. |
| 7,476,077 B2 | 1/2009 | Woodard et al. |
| 7,491,163 B2 | 2/2009 | Viole et al. |
| 7,575,423 B2 | 8/2009 | Wampler |
| 7,591,777 B2 | 9/2009 | LaRose |
| 7,645,225 B2 | 1/2010 | Medvedev et al. |
| 7,660,635 B1 | 2/2010 | Verness et al. |
| 7,699,586 B2 | 4/2010 | LaRose et al. |
| 7,731,675 B2 | 6/2010 | Aboul-Hosn et al. |
| 7,748,964 B2 | 7/2010 | Yaegashi et al. |
| 7,802,966 B2 | 9/2010 | Wampler et al. |
| 7,841,976 B2 | 11/2010 | McBride et al. |
| 7,850,594 B2 | 12/2010 | Sutton et al. |
| 7,887,479 B2 | 2/2011 | LaRose et al. |
| 7,888,242 B2 | 2/2011 | Tanaka et al. |
| 7,934,909 B2 | 5/2011 | Nuesser et al. |
| 7,972,122 B2 | 7/2011 | LaRose et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,152,493 B2 | 4/2012 | LaRose et al. |
| 8,177,703 B2 | 5/2012 | Smith et al. |
| 8,226,373 B2 | 7/2012 | Yaehashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,506,470 B2 | 8/2013 | LaRose et al. |
| 8,512,012 B2 | 8/2013 | Mustafa et al. |
| 8,535,211 B2 | 9/2013 | Campbell et al. |
| 8,585,290 B2 | 11/2013 | Bauer |
| 8,613,696 B2 | 12/2013 | Medvedev et al. |
| 8,652,024 B1 | 2/2014 | Yanai et al. |
| 8,686,674 B2 | 4/2014 | Bi et al. |
| 8,770,945 B2 | 7/2014 | Ozaki et al. |
| 8,821,365 B2 | 9/2014 | Ozaki et al. |
| 8,827,661 B2 | 9/2014 | Mori |
| 8,840,538 B2 | 9/2014 | Jeffery et al. |
| 8,864,644 B2 | 10/2014 | Yomtov |
| 8,870,552 B2 | 10/2014 | Ayre et al. |
| 8,880,450 B2 | 11/2014 | Dobson et al. |
| 8,882,744 B2 | 11/2014 | Dormanen et al. |
| 8,897,873 B2 | 11/2014 | Schima et al. |
| 8,968,174 B2 | 3/2015 | Yanai et al. |
| 9,067,005 B2 | 6/2015 | Ozaki et al. |
| 9,068,572 B2 | 6/2015 | Ozaki et al. |
| 9,089,635 B2 | 7/2015 | Reichenbach et al. |
| 9,109,601 B2 | 8/2015 | Mori |
| 9,132,215 B2 | 9/2015 | Ozaki et al. |
| 9,133,854 B2 | 9/2015 | Okawa et al. |
| 9,371,826 B2 | 6/2016 | Yanai et al. |
| 9,381,285 B2 | 7/2016 | Ozaki et al. |
| 9,382,908 B2 | 7/2016 | Ozaki et al. |
| 9,410,549 B2 | 8/2016 | Ozaki et al. |
| 2001/0039369 A1 | 11/2001 | Terentiev |
| 2002/0051711 A1 | 5/2002 | Ozaki |
| 2002/0058994 A1 | 5/2002 | Hill et al. |
| 2002/0094281 A1 | 7/2002 | Khanwilkar et al. |
| 2002/0095210 A1 | 7/2002 | Finnegan et al. |
| 2003/0023302 A1 | 1/2003 | Moe et al. |
| 2003/0045772 A1 | 3/2003 | Reich et al. |
| 2003/0072656 A1 | 4/2003 | Niwatsukino et al. |

(56) References Cited

U.S. PATENT DOCUMENTS

| | | |
|---|---|---|
| 2003/0144574 A1 | 7/2003 | Heilman et al. |
| 2003/0199727 A1 | 10/2003 | Burke |
| 2004/0007515 A1 | 1/2004 | Geyer |
| 2004/0015232 A1 | 1/2004 | Shu et al. |
| 2004/0024285 A1 | 2/2004 | Muckter |
| 2004/0030381 A1 | 2/2004 | Shu |
| 2004/0143151 A1 | 7/2004 | Mori et al. |
| 2004/0145337 A1 | 7/2004 | Morishita |
| 2004/0152944 A1 | 8/2004 | Medvedev et al. |
| 2004/0171905 A1 | 9/2004 | Yu et al. |
| 2004/0210305 A1 | 10/2004 | Shu et al. |
| 2004/0263341 A1 | 12/2004 | Enzinna |
| 2005/0008496 A1 | 1/2005 | Tsubouchi et al. |
| 2005/0025630 A1 | 2/2005 | Ayre et al. |
| 2005/0073273 A1 | 4/2005 | Maslov et al. |
| 2005/0089422 A1 | 4/2005 | Ozaki et al. |
| 2005/0131271 A1 | 6/2005 | Benkowski et al. |
| 2005/0141887 A1 | 6/2005 | Lelkes |
| 2005/0194851 A1 | 9/2005 | Eckert et al. |
| 2005/0261542 A1 | 11/2005 | Abe et al. |
| 2005/0287022 A1 | 12/2005 | Yaegashi et al. |
| 2006/0024182 A1 | 2/2006 | Akdis et al. |
| 2006/0055274 A1 | 3/2006 | Kim |
| 2006/0127227 A1 | 6/2006 | Mehlhorn et al. |
| 2007/0073393 A1 | 3/2007 | Kung et al. |
| 2007/0078293 A1 | 4/2007 | Shambaugh, Jr. |
| 2007/0095648 A1 | 4/2007 | Wampler et al. |
| 2007/0114961 A1 | 5/2007 | Schwarzkopf |
| 2007/0134993 A1 | 6/2007 | Tamez et al. |
| 2007/0189648 A1 | 8/2007 | Kita et al. |
| 2007/0213690 A1 | 9/2007 | Phillips et al. |
| 2007/0231135 A1 | 10/2007 | Wampler et al. |
| 2007/0282298 A1 | 12/2007 | Mason |
| 2007/0297923 A1 | 12/2007 | Tada |
| 2008/0007196 A1 | 1/2008 | Tan et al. |
| 2008/0021394 A1 | 1/2008 | La Rose et al. |
| 2008/0030895 A1 | 2/2008 | Obara et al. |
| 2008/0124231 A1 | 5/2008 | Yaegashi |
| 2008/0183287 A1 * | 7/2008 | Ayre ............... A61M 1/101 623/3.28 |
| 2008/0211439 A1 | 9/2008 | Yokota et al. |
| 2009/0041595 A1 | 2/2009 | Garzaniti et al. |
| 2009/0060743 A1 | 3/2009 | McBride et al. |
| 2009/0074336 A1 | 3/2009 | Engesser et al. |
| 2009/0171136 A1 | 7/2009 | Shambaugh, Jr. |
| 2009/0257693 A1 | 10/2009 | Aiello |
| 2010/0185280 A1 | 7/2010 | Ayre et al. |
| 2010/0222634 A1 | 9/2010 | Poirier |
| 2010/0256440 A1 | 10/2010 | Maher |
| 2010/0266423 A1 | 10/2010 | Gohean et al. |
| 2010/0305692 A1 | 12/2010 | Thomas et al. |
| 2011/0015732 A1 | 1/2011 | Kanebako |
| 2011/0112354 A1 | 5/2011 | Nishimura et al. |
| 2011/0118766 A1 | 5/2011 | Reichenbach et al. |
| 2011/0118829 A1 | 5/2011 | Hoarau et al. |
| 2011/0118833 A1 | 5/2011 | Reichenbach et al. |
| 2011/0129373 A1 | 6/2011 | Mori |
| 2011/0218383 A1 | 9/2011 | Broen et al. |
| 2011/0218384 A1 | 9/2011 | Bachman et al. |
| 2011/0218385 A1 | 9/2011 | Bolyare et al. |
| 2011/0243759 A1 | 10/2011 | Ozaki et al. |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0022645 A1 | 1/2012 | Burke |
| 2012/0035411 A1 | 2/2012 | LaRose et al. |
| 2012/0078030 A1 | 3/2012 | Bourque |
| 2012/0095281 A1 | 4/2012 | Reichenbach et al. |
| 2012/0130152 A1 | 5/2012 | Ozaki et al. |
| 2012/0226350 A1 | 9/2012 | Ruder et al. |
| 2012/0243759 A1 | 9/2012 | Fujisawa |
| 2012/0253103 A1 | 10/2012 | Jarvik |
| 2012/0308363 A1 | 12/2012 | Ozaki et al. |
| 2013/0030240 A1 | 1/2013 | Schima et al. |
| 2013/0121821 A1 | 5/2013 | Ozaki et al. |
| 2013/0158521 A1 | 6/2013 | Sobue |
| 2013/0170970 A1 | 7/2013 | Ozaki et al. |
| 2013/0178694 A1 | 7/2013 | Jeffery et al. |
| 2013/0243623 A1 | 9/2013 | Okawa et al. |
| 2013/0289334 A1 | 10/2013 | Badstibner et al. |
| 2014/0030122 A1 | 1/2014 | Ozaki et al. |
| 2014/0066690 A1 | 3/2014 | Siebenhaar et al. |
| 2014/0066691 A1 | 3/2014 | Siebenhaar |
| 2014/0100413 A1 | 4/2014 | Casas et al. |
| 2014/0142367 A1 | 5/2014 | Ayre et al. |
| 2014/0200389 A1 | 7/2014 | Yanai et al. |
| 2014/0205467 A1 | 7/2014 | Yanai et al. |
| 2014/0241904 A1 | 8/2014 | Yanai et al. |
| 2014/0275721 A1 | 9/2014 | Yanai et al. |
| 2014/0275727 A1 | 9/2014 | Bonde et al. |
| 2014/0296615 A1 | 10/2014 | Franano |
| 2014/0309481 A1 | 10/2014 | Medvedev et al. |
| 2014/0314597 A1 | 10/2014 | Allaire et al. |
| 2014/0323796 A1 | 10/2014 | Medvedev et al. |
| 2015/0017030 A1 | 1/2015 | Ozaki |
| 2015/0023803 A1 | 1/2015 | Fritz et al. |
| 2015/0078936 A1 | 3/2015 | Mori |
| 2015/0306290 A1 * | 10/2015 | Rosenberg ........ A61B 5/6869 600/17 |
| 2015/0374892 A1 | 12/2015 | Yanai et al. |
| 2016/0058930 A1 | 3/2016 | Medvedev et al. |

FOREIGN PATENT DOCUMENTS

| | | |
|---|---|---|
| CN | 102239334 A | 11/2011 |
| CN | 102341600 A | 2/2012 |
| EP | 2945662 B1 | 9/1999 |
| EP | 971212 A | 1/2000 |
| EP | 1113117 A2 | 7/2001 |
| EP | 1327455 A | 7/2003 |
| EP | 1430919 A1 | 6/2004 |
| EP | 1495773 A2 | 1/2005 |
| EP | 1598087 A2 | 3/2005 |
| EP | 1526286 A1 | 4/2005 |
| EP | 1565231 A2 | 8/2005 |
| EP | 1495773 A3 | 11/2006 |
| EP | 1495773 B1 | 2/2009 |
| EP | 1469770 B1 | 10/2010 |
| EP | 1105172 B1 | 2/2011 |
| EP | 2292282 A1 | 3/2011 |
| EP | 2298375 A1 | 3/2011 |
| EP | 2372160 A1 | 10/2011 |
| EP | 2405140 A1 | 1/2012 |
| EP | 2405141 A1 | 1/2012 |
| EP | 2461465 A1 | 6/2012 |
| EP | 2538086 A1 | 12/2012 |
| EP | 2554191 A1 | 2/2013 |
| EP | 2594799 A1 | 5/2013 |
| EP | 2618001 A1 | 7/2013 |
| EP | 2665499 A1 | 11/2013 |
| EP | 2693609 A1 | 2/2014 |
| EP | 2948202 A1 | 12/2015 |
| EP | 2961987 A1 | 1/2016 |
| EP | 3013385 A2 | 5/2016 |
| JP | 58/9535 | 1/1983 |
| JP | 61/293146 | 12/1986 |
| JP | H02-007780 U | 1/1990 |
| JP | H02-033590 U | 3/1990 |
| JP | 04/091396 A | 3/1992 |
| JP | 04/148094 A | 5/1992 |
| JP | 05/021197 U | 3/1993 |
| JP | 06/014538 U | 2/1994 |
| JP | 06/053790 U | 7/1994 |
| JP | 2006/070476 | 9/1994 |
| JP | 2006/245455 | 9/1994 |
| JP | 07/014220 U | 3/1995 |
| JP | 07/042869 U | 8/1995 |
| JP | 07/509156 A | 10/1995 |
| JP | 09/122228 A | 5/1997 |
| JP | 10/331841 A | 12/1998 |
| JP | 11/244377 A | 9/1999 |
| JP | 2001/309628 | 11/2001 |
| JP | 2003/135592 A | 5/2003 |
| JP | 2004/166401 A | 6/2004 |

(56) References Cited

FOREIGN PATENT DOCUMENTS

| | | |
|---|---|---|
| JP | 2004/209240 A | 7/2004 |
| JP | 2004/332566 A | 11/2004 |
| JP | 2004/346925 A | 12/2004 |
| JP | 2005/094955 | 4/2005 |
| JP | 2005/127222 A | 5/2005 |
| JP | 2005/245138 | 9/2005 |
| JP | 2005/270345 A | 10/2005 |
| JP | 2005/270415 A | 10/2005 |
| JP | 2005/287599 A | 10/2005 |
| JP | 2006/167173 A | 6/2006 |
| JP | 2007/002885 A | 1/2007 |
| JP | 2007/043821 | 2/2007 |
| JP | 2007/089972 A | 4/2007 |
| JP | 2007/089974 | 4/2007 |
| JP | 2007/215292 | 8/2007 |
| JP | 2007/247489 | 9/2007 |
| JP | 2008/011611 | 1/2008 |
| JP | 2008/104278 | 5/2008 |
| JP | 2008/132131 | 6/2008 |
| JP | 2008/99453 | 8/2008 |
| JP | 2008/193838 | 8/2008 |
| JP | 2008/297997 A | 12/2008 |
| JP | 2008/301634 | 12/2008 |
| JP | 2006/254619 | 9/2009 |
| JP | 2010/133381 A | 6/2010 |
| JP | 2010/136863 A | 6/2010 |
| JP | 2010/203398 A | 9/2010 |
| JP | 2010/209691 A | 9/2010 |
| JP | 2011/169166 A | 9/2011 |
| JP | 2012/021413 | 2/2012 |
| JP | 2012/062790 A | 3/2012 |
| JP | 5171953 B2 | 3/2013 |
| JP | 5572832 B2 | 8/2014 |
| JP | 5656835 B2 | 1/2015 |
| WO | 93/07388 A1 | 4/1993 |
| WO | 94/14226 | 6/1994 |
| WO | 96/31934 | 10/1996 |
| WO | 97/42413 A1 | 11/1997 |
| WO | 00/64509 A1 | 11/2000 |
| WO | 2004/098677 A1 | 11/2004 |
| WO | 2005/011087 A1 | 2/2005 |
| WO | 2005/028000 A1 | 3/2005 |
| WO | 2005/034312 A2 | 4/2005 |
| WO | 2009/157408 A1 | 12/2009 |
| WO | 2010/067682 A1 | 6/2010 |
| WO | 2010/101082 A1 | 9/2010 |
| WO | 2010/101107 A1 | 9/2010 |
| WO | 2011/013483 A1 | 2/2011 |
| WO | 2012/040544 A1 | 3/2012 |
| WO | 2012/047550 A1 | 4/2012 |
| WO | 2012/132850 A1 | 10/2012 |
| WO | 2014/044287 A1 | 3/2014 |
| WO | 2014/113533 A1 | 7/2014 |
| WO | 2014/116676 A1 | 7/2014 |
| WO | 2014/133942 A1 | 9/2014 |
| WO | 2014/179271 A2 | 11/2014 |
| WO | 2016/033131 A1 | 3/2016 |
| WO | 2016/033133 A1 | 3/2016 |
| WO | 2016033133 | 3/2016 |

OTHER PUBLICATIONS

Asama, J., et al.,"A New Design for a Compact Centrifugal Blood Pump with a Magnetically Levitated Rotor", Asaio Jopurnal, vol. 50, No. 6, Nov. 1, 2004 (Nov. 1, 2004), pp. 550-556.
Asama, et al., "Suspension Performance of a Two-Axis Actively Regulated Consequent-Pole Bearingless Motor," IEEE Transactions on Energy Conversion, vol. 28, No. 4, Dec. 2013, 8 pages.
European Search report Issued in European Patent Application No. 10748702.7, mailed Apr. 2, 2013.
Extended European Search Report issued in European Patent Application No. EP 10748677.1, mailed Nov. 19, 2012.
Extended European Search Report issued in European Patent Application No. EP 11825062.0, mailed Jun. 18, 2015, all pages.
Extended European Search Report issued in European Patent Application No. EP 11806627.3, mailed Oct. 8, 2014, all pages.
Extended European Search Report issued on Mar. 26, 2015 in European Patent Application No. EP 09770118.9 filed Jun. 22, 2009, all pages.
International Search Report (PCT/ISA/210) issued on Jul. 14, 2009, by Japanese Patent Office as the International Searching Authority for International Application No. PCT/JP2009/061318.
International Search Report and Written Opinion issued in PCT/JP2011/050925, mailed Apr. 12, 2011.
International Search Report and Written Opinion issued in PCT/JP2011/054134, mailed Apr. 12, 2011.
International Search Report and Written Opinion issued in PCT/JP2011/064768, mailed Sep. 13, 2011.
International Search Report and Written Opinion issued in PCT/JP2011/070450, mailed Dec. 13, 2011.
International Search Report and Written Opinion of PCT/US2014/012448 mailed on Feb. 19, 2014, all pages.
International Search Report and Written Opinion of PCT/US2014/011786 mailed on May 5, 2014, all pages.
International Search Report and Written Opinion of PCT/US2014/012502 dated May 9, 2014, all pages.
International Search Report and Written Opinion of PCT/US2014/012511 mailed on May 14, 2014, all pages.
International Search Report and Written Opinion of PCT/US2014/017932 mailed on Jun. 16, 2014, all pages.
International Preliminary Report on Patentability mailed on Aug. 6, 2015 for International Patent Application No. PCT/US2014/012511 filed on Jan. 22, 2014, all pages.
International Preliminary Report on Patentability mailed on Aug. 6, 2015 for International Patent Application No. PCT/US2014/012502 filed on Jan. 22, 2014, all pages.
International Preliminary Report on Patentability mailed on Feb. 25, 2016 for International Patent Application No. PCT/US2014/035798 filed on Apr. 29, 2014, all pages.
Kosaka, et al., "Operating Point Control Systemt for a Continuous Flow Artificial Heart: In Vitro Study," ASAIO Journal 2003, all pages.
Neethu, S., et al., "Novel design, optimization and realization of axial flux motor for implantable blood pump", Power Electronics, Drives and Energy Systems (PEDES) & 2010 Power Indian, 2010 Joint International Conference on, IEEE, Dec. 20, 2010 (Dec. 20, 2010), pp. 1-6.
Sandtner, J., et al., "Electrodynamic Passive Magnetic Bearing with Planar Halbach Arrays", Aug. 6, 2004 (Aug. 6, 2004), retrieved from the internet: <http://www.silphenix.ch/lexington.pdf>, all pages.
Supplementary European Search Report issued in European Application No. 09831788.6, dated Jan. 7, 2013, 7 pages.
Terumo Heart, Inc., "Handled With Care—Significantly Reduce the Risk of Cell Damage," Terumo brochure, Apr. 2010, 2 pages.
Yamazaki, et al., "Development of a Miniature Intraventricular Axial Flow Blood Pump," ASAIO Journal, 1993, 7 pages.
Slaughter et al., "Clinical Management of Continuous-Flow Left Ventricular Assist Devices in Advanced Heart Failure," The Journal of Heart and Lung Transplantation, vol. 29, No. 4S, Apr. 2010, 39 pages.
Antonio Luiz S. Ferreira, "A Rule-Based Controller Based on Suction Detection for Rotary Blood Pumps," University of Pittsburgh School of Engineering, Jul. 2007, 178 pages.
International Patent Application No. PCT/US2015/046846, International Search Report and Written Opinion, mailed on Oct. 27, 2015, 8 pages.
European office action mailed on Jan. 27, 2016 for EP 10804230.0, all pages.
Extended European Search Report mailed on Feb. 4, 2016 in European Patent Application No. EP 12764433.4, filed Mar. 12, 2012, all pages.
International Preliminary Report on Patentability mailed on Jul. 30, 2015 for International Patent Application No. PCT/US2014/011786, filed on Jan. 16, 2014, all pages.
International Search Report and Written Opinion of PCT/US2014/012511, mailed on May 147, 2014, all pages.

(56) References Cited

OTHER PUBLICATIONS

International Search Report and Written Opinion of PCT/US2014/017932, mailed on Jun. 16, 2014, all pages.
International Preliminary Report on Patentability mailed on Sep. 11, 2015 for International Patent Application No. PCT/US2014/017932, filed on Feb. 24, 2014, all pages.
International Search Report and Written Opinion of PCT/US2014/035798, mailed on Feb. 11, 2016, all pages.
International Search Report and Written Opinion of PCT/US2016/017611, mailed on May 16, 2016, all pages.
International Search Report and Written Opinion of PCT/US2016/017791, mailed on May 16, 2016, all pages.
Japanese office action mailed on Dec. 11, 2015 JP 2013-507344, all pages.
International Search Report and Written Opinion of PCT/US2016/017812, mailed on Jun. 7, 2016, all pages.
International Search Report and Written Opinion of PCT/US2016/017864, mailed Jun. 8, 2016, all pages.
Decision to Grant for JP 2013-507344 issued Jun. 14, 2016, all pages.

* cited by examiner

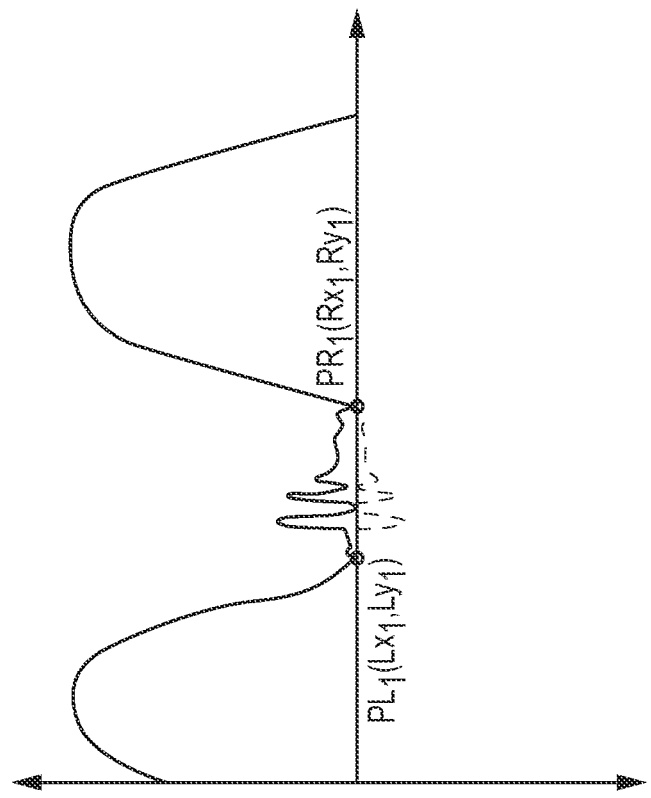
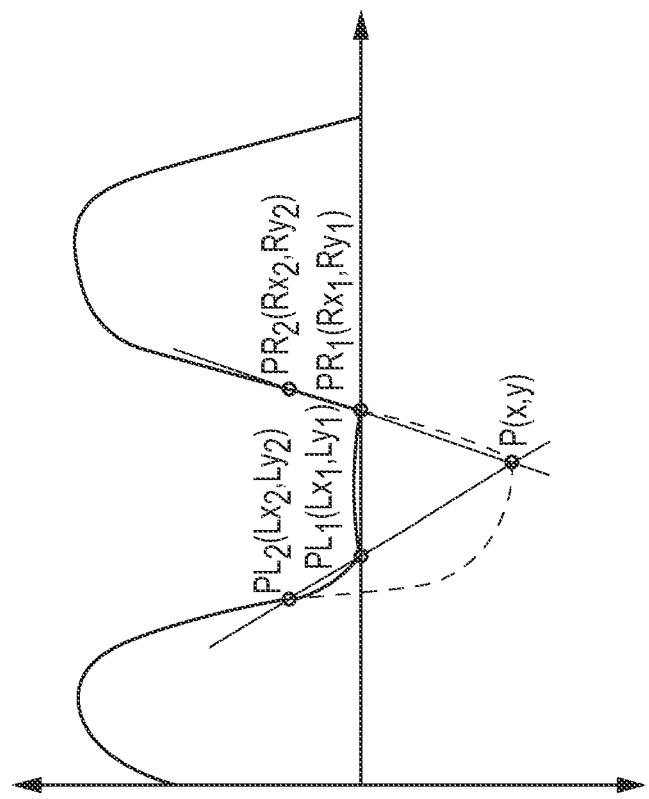
FIG.6A
FIG.6B

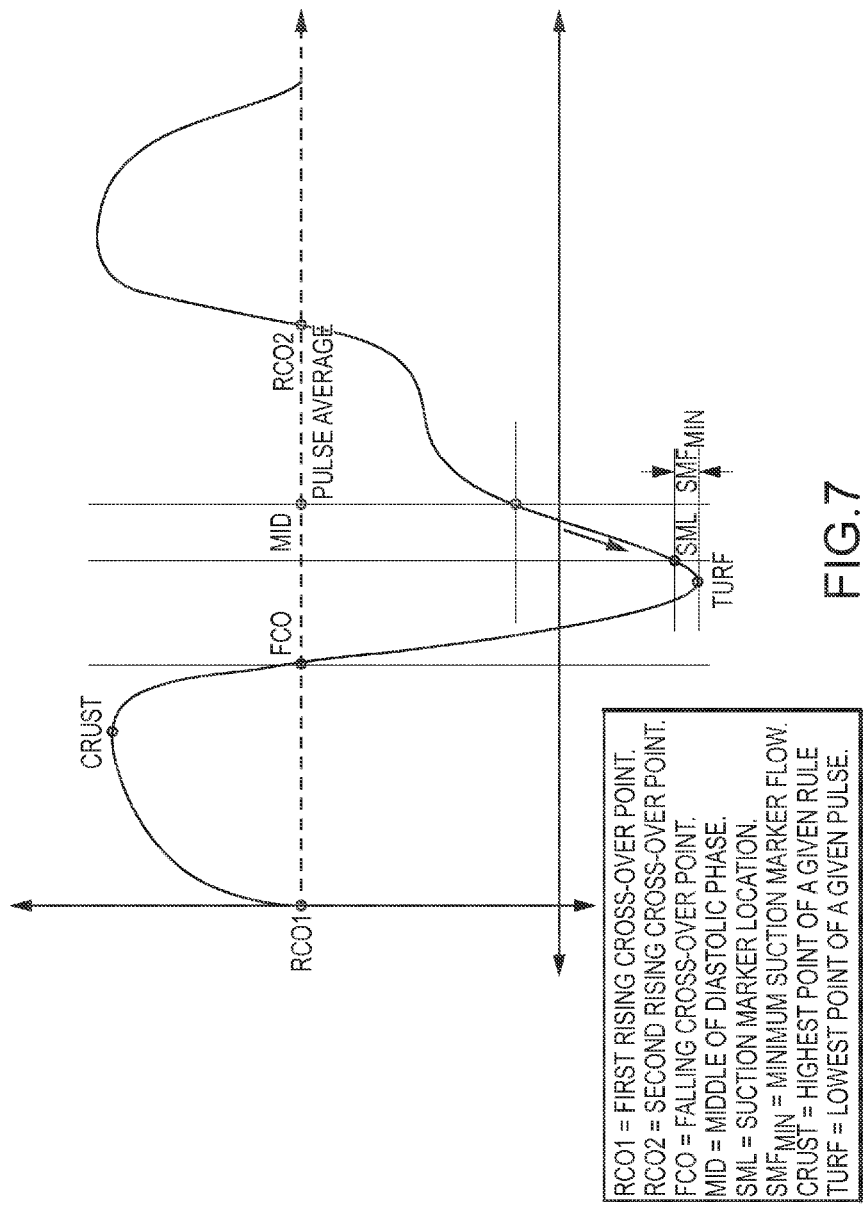

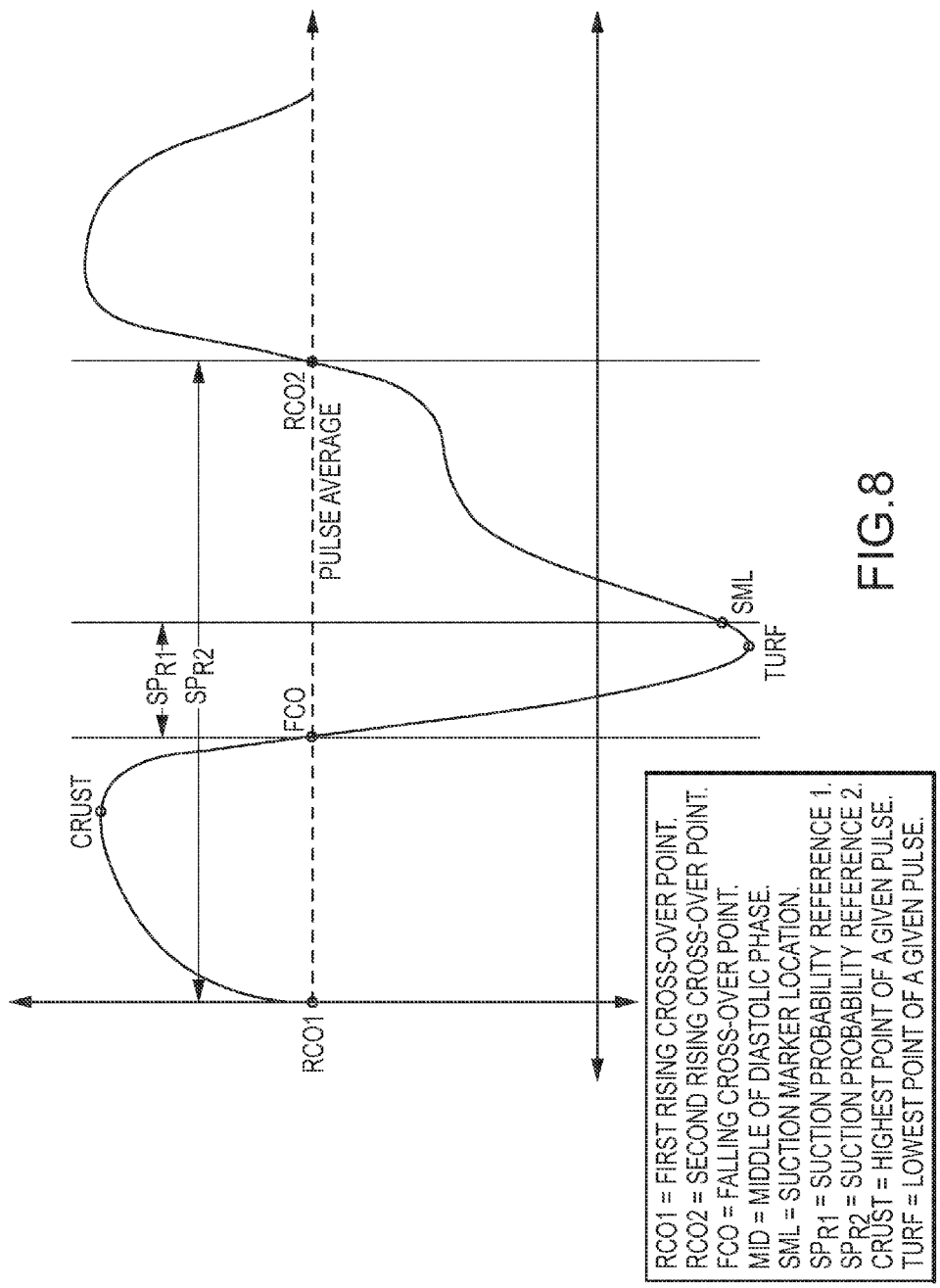

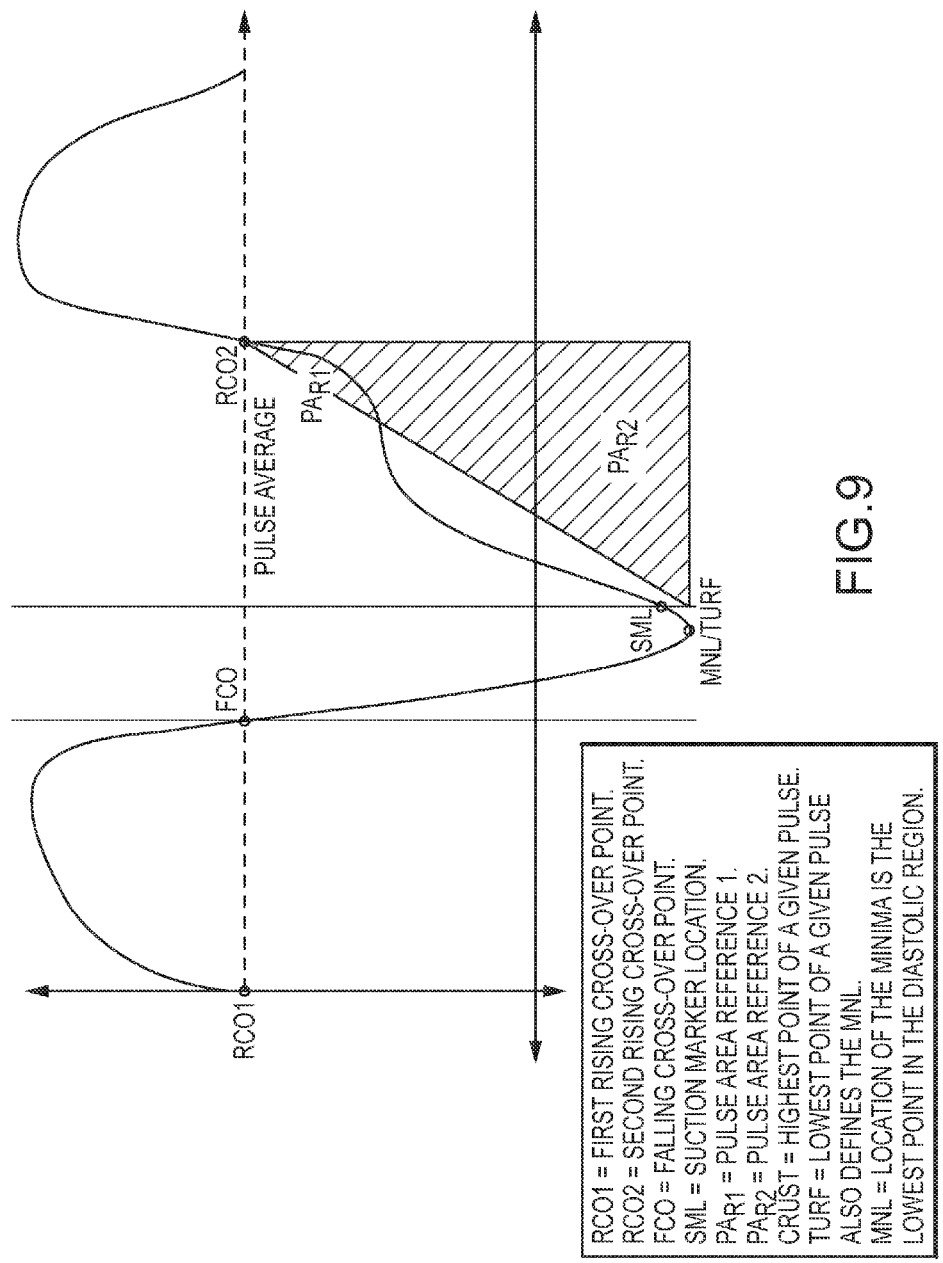

BLOOD PUMP AND METHOD OF SUCTION DETECTION

CROSS REFERENCE TO RELATED APPLICATIONS

This application claims priority to Provisional U.S. Patent Application No. 62/041,910 filed Aug. 26, 2014, entitled "BLOOD PUMP AND METHOD OF SUCTION DETECTION," entire disclosure of which is hereby incorporated by reference, for all purposes, as if fully set forth herein.

BACKGROUND OF THE INVENTION

This invention relates, in general, to mechanical circulatory support systems and methods for their use. Various aspects of the invention relate to methods of detecting and mitigating ventricular suction events.

Suction detection and prevention is critical for heart failure patients supported by blood pumps (e.g. a ventricular assist device or VAD). In the case of a VAD, a suction event refers to an instance of negative pressure created in the ventricle. A suction event, which is typically triggered by a pump speed too high for the given systemic conditions and a patient's physiology, affects clinical outcomes and can lead to major adverse events in extreme cases. Suction events can be avoided by lowering the pump speed when such an event is detected. A speed reduction may not completely prevent suction, but it will reduce the likelihood of a continuous severe suction condition under normal pump operation.

One typical method for detecting a suction event includes the trend analysis of a pulsatility index (PI). PI is a measure of the variability of blood velocity in a vessel, and in the case of a VAD, PI is a measure of the pressure differential inside the VAD pump during the native heart's cardiac cycle and represents volume status, right ventricle function, and native heart contractility. PI may be calculated taking into consideration factors such as pump power, current, back electromotive force (emf). Another method for detecting a suction event includes correlating the pump flow waveform to a database of signals indicating suction events. Yet another method includes performing a harmonic analysis of the pump power or pump flow waveform. Exemplars of existing suction detection techniques are described in U.S. Pat. No. 7,645,225 to Medvedev, U.S. Pat. No. 7,175,588 to Morello, U.S. Pat. No. 6,991,595 to Burke et al., and U.S. Pat. No. 5,888,242 to Antaki et al. and U.S. Pub. No. 2014/0100413 to Casas, which are incorporated herein for all purposes by reference.

Existing methods for detecting the imminence or presence of a suction event have several limitations.

Methods other than waveform correlation are limited in their capability to discern a suction event when compared to other patient physiological conditions that may not have any relevance to a suction condition (U.S. Pub. No. 2014/0100413 to Casas). Accordingly, the results can be inaccurate and lead to false positive detection of a suction event. Although waveform correlation methods can be more accurate, these techniques are challenging to implement because they require a database of suction event signals against the input signal be matched (U.S. Pat. No. 7,175,588 to Morello). The correlation of signals also requires extensive signal processing capabilities. Such capabilities are typically not available in embedded systems used to drive LVAD pumps. Extensive signal processing also tends to lead to greater energy usage and heat which can be challenging when the components are implanted in the body or directly against the skin.

What is needed are devices and methods which overcome the above disadvantages. What is needed is an improved suction detection technique.

BRIEF SUMMARY OF THE INVENTION

In summary, one aspect of the present invention is directed to estimating a flow rate of a blood pump by interpolating data sets defining pump power to flow for various pump speed values. In various embodiments, the method includes solving a quadratic equation for the current pump speed.

Various aspects of the invention are directed to a method of detecting a suction event of a blood pump, comprising estimating a flow rate of the pump; identifying pulses in the flow rate based on the estimated flow; estimating a negative flow based on a valid identification of a pulse; and evaluating a characteristic of the pulse for an existence of a suction condition. In various embodiments, the evaluation comprises locating a suction marker reference point based on a midpoint in the diastolic phase; identifying a suction marker location where a suction marker flow minimum is reached; and using the suction marker location to identify a probability of a suction condition.

In one particular aspect, the flow is estimated by solving for the following quadratic equation:

$$F=Ap^2+Bp+C$$

Where,
F=Flow Rate (LPM)
p=Pump Power (W) adjusted for hematocrit (This could also be based on current)
A=Interpolated X2 Polynomial coefficient for the given pump speed.
B=Interpolated X1 Polynomial coefficient for the given pump speed.
C=Interpolated X0 Polynomial coefficient for the given pump speed.

In still another aspect, the pulse segmentation may include: The Pulse Average, The Pulse Minima (Turf), The Pulse Maxima (Crest), The pulse falling cross-over point, The Systolic Average (SSA), The Diastolic Average (DSA), The Systolic Pulse Index (SPI), The Diastolic Pulse Index (DPI), The Pulse Flow Index (PFI), The Negative Flow Correction, The Pulse Asymmetry Index, The Pulse Suction Index ($\Psi$), The Pulse Duty Cycle (PDC), The Pulse Frequency (PHZ), and a combination of the same.

Another aspect of the present invention is directed to a system for controlling a blood pump comprising a pump flow estimator for estimating flow rate of the pump, a pump pulse detector for detecting a pulse based on flow estimator output, a negative flow estimator for approximating a negative flow and adjusting a signal from the pulse detector when a valid pulse is detected by the pulse detector, a fault generator for providing notifications to a patient when an invalid pulse is detected by the pulse detector, and a suction detector for evaluating the probability of a suction event based on at least one characteristic of the signal output from the negative flow estimator. In various embodiments, the system further comprises a speed controller for adjusting a speed of the pump to prevent or mitigate the suction condition.

The systems and methods of the present invention have other features and advantages which will be apparent from or are set forth in more detail in the accompanying drawings, which are incorporated in and form a part of this specification, and the following Detailed Description of the Invention, which together serve to explain the principles of the present invention.

BRIEF DESCRIPTION OF THE DRAWINGS

FIG. 6A and FIG. 6B are line charts showing the method for negative flow approximation in accordance with the invention.

FIG. 7 is a line chart showing the method for identifying the suction marker location (SML) for evaluating the probability of a suction condition in accordance with the invention.

FIG. 8 is another line chart showing the method for evaluating the probability of a suction condition in accordance with the invention.

FIG. 9 is yet another line chart showing the method for evaluating the probability of a suction condition in accordance with the invention.

TERMS AND DEFINITIONS

Figure 1:
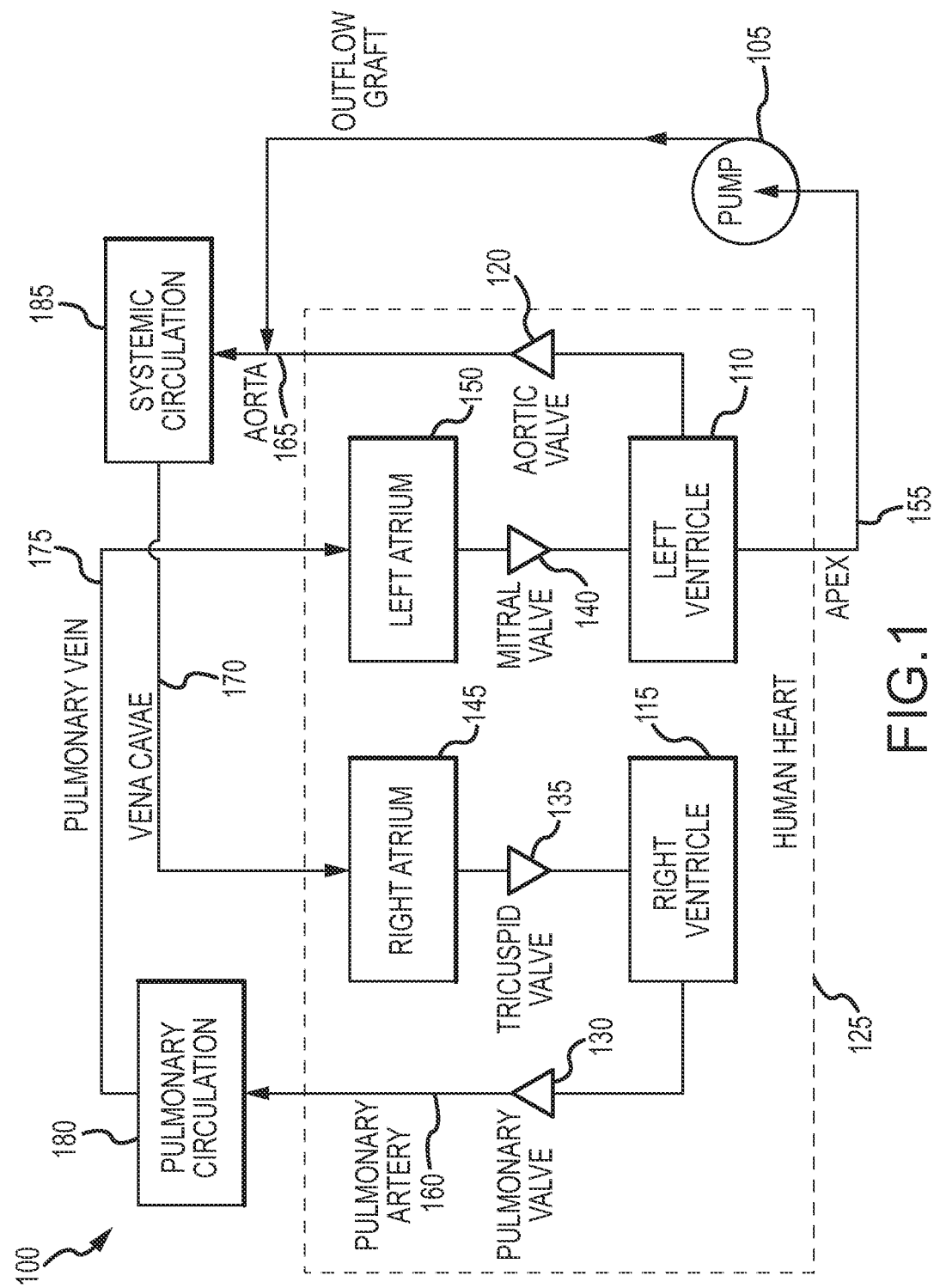
FIG. 1 is a schematic of a system for controlling a blood pump in accordance with the present invention.

Waveform Asymmetry Index (WAI) (%)—First Min, Mean and Max of estimated pump flow (EPF) over a time period are calculated and then WAI is calculated using the formula, WAI=100*(MEAN(EPF)−MIN(EPF))/(MAX(EPF)−MEAN(EPF)).

Systolic Average (SSA) (LPM)—First crest of the estimated pump flow (EPF) is identified and then average is calculated from start to the crest of the Pulse.

Pulse Diastolic Average (DSA) (LPM)—First falling cross-over and the turf of the estimated pump flow (EPF) are identified and then average is calculated from the falling cross-over to the turf of the Pulse.

Pulse Flow Index (PFI) (%)—First Pulse DSA and SSA are evaluated and then PFI is calculated using the formula, PFI=(100*DSA)/SSA.

Pulse Asymmetry Index (PAI) (%)—First Min(Pulse), Mean(Pulse) and Max(Pulse) flow for each pulse is evaluated. Then PAI is calculated for each pulse using the formula, PAI=100*(MEAN(Pulse)−MIN(Pulse))/(MAX(Pulse)−MEAN(Pulse)). Then PAI is calculated by averaging PAI of most recent data.

Pulse Duty Cycle (PDC) (%)—First PDC for individual pulse is evaluated using the formula, PDC=100*(Falling Cross-over Pulse Sample)/(Total Number of Pulse Samples). Then PDC is calculated by averaging PDC of most recent data.

Pulse Frequency (PHZ) (Hz)—First PHZ for individual pulse is evaluated using the formula, PHZ=100/(Total Number of Pulse Samples). Then PHZ is calculated by averaging PHZ of most recent data.

Pulses per Minute (PPM)—First PHZ is evaluated and then PPM is calculated using the formula, PPM=60*(PHZ).

Systolic Pulse Index (SPI)—In the systolic segment of the pulse, first rising cross-over, falling cross-over and the marker in the neighborhood of maxima of the EPF pulse are identified and then area from rising cross-over to marker and from the marker to the falling cross-over is calculated. Ratio of these terms provides the Inner Systolic Pulse Index. Furthermore, the Outer Systolic Pulse Index is calculated by calculating the ratio of the area outside the pulse under a bounded rectangle. Note that this term is identified here but not used for suction condition as the Pulse Suction Index (PSI) is found to be a better measure of suction event detection.

Diastolic Pulse Index (DPI)—In the diastolic segment of the pulse, the falling cross-over, rising cross-over and the marker in the neighborhood of minima of the EPF pulse are identified and then area from falling cross-over to marker and from the marker to the rising cross-over is calculated. Ratio of these terms provides the Inner Diastolic Pulse Index. Furthermore, the Outer Diastolic Pulse Index is calculated by calculating the ratio of the area outside the pulse under a bounded rectangle. Note that this term is identified here but not used for suction condition as the Pulse Suction Index (PSI) is found to be a better measure of suction event detection.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

For example, any detail discussed with regard to one embodiment may or may not be present in all contemplated versions of that embodiment. Likewise, any detail discussed with regard to one embodiment may or may not be present in all contemplated versions of other embodiments discussed herein. Finally, the absence of discussion of any detail with regard to embodiment herein shall be an implicit recognition that such detail may or may not be present in any version of any embodiment discussed herein.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "machine-readable medium" includes, but is not limited to transitory and non-transitory, portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

For convenience in explanation and accurate definition in the appended claims, the terms "up" or "upper", "down" or "lower", "inside" and "outside" are used to describe features of the present invention with reference to the positions of such features as displayed in the figures.

Turning now to the drawings, wherein like components are designated by like reference numerals throughout the various figures, attention is directed to FIGS. 1 to 9. Various aspects are similar to those described in and U.S. Pub. Nos. 2014/0100413 to Casas, 2011/0129373 to Mori, 2014/0155682 to Jeffery et al., and 2013/0225909 to Dormanen et al., and U.S. Pat. No. 7,850,594 to Sutton, U.S. Pat. No. 7,645,225 to Medvedev, U.S. Pat. No. 7,175,588 to Morello, U.S. Pat. No. 6,991,595 to Burke et al., U.S. Pat. No. 5,888,242 to Antaki et al., and U.S. Pat. No. 6,066,086 to Antaki et al., the entire contents of which patents and applications are incorporated herein for all purposes by reference.

As shown in FIG. 1, in various embodiments, the basic design concept 100 includes a pump 105 connected to the left ventricle 110 (or right ventricle 115 or both ventricles) across the aortic valve 120 of a heart 125. The flow through pump 105 is estimated using pump parameters which include power/current, speed and a flow map, which allows transformation of inputs like power/current and speed to flow derived from the pump flow characteristics curves (e.g. power/current-flow curves for various speeds and viscosities/hematocrits). Heart 125 also includes pulmonary valve 130, tricuspid valve 135, mitral valve 140, right atrium 145, and left atrium 150. Apex 155, pulmonary artery 160, aorta 165, vena cavae 170, and pulmonary vein 175 are also shown in FIG. 1. Blocks representing pulmonary circulation 180 and systemic circulation 185 are also shown.

Figure 2A:
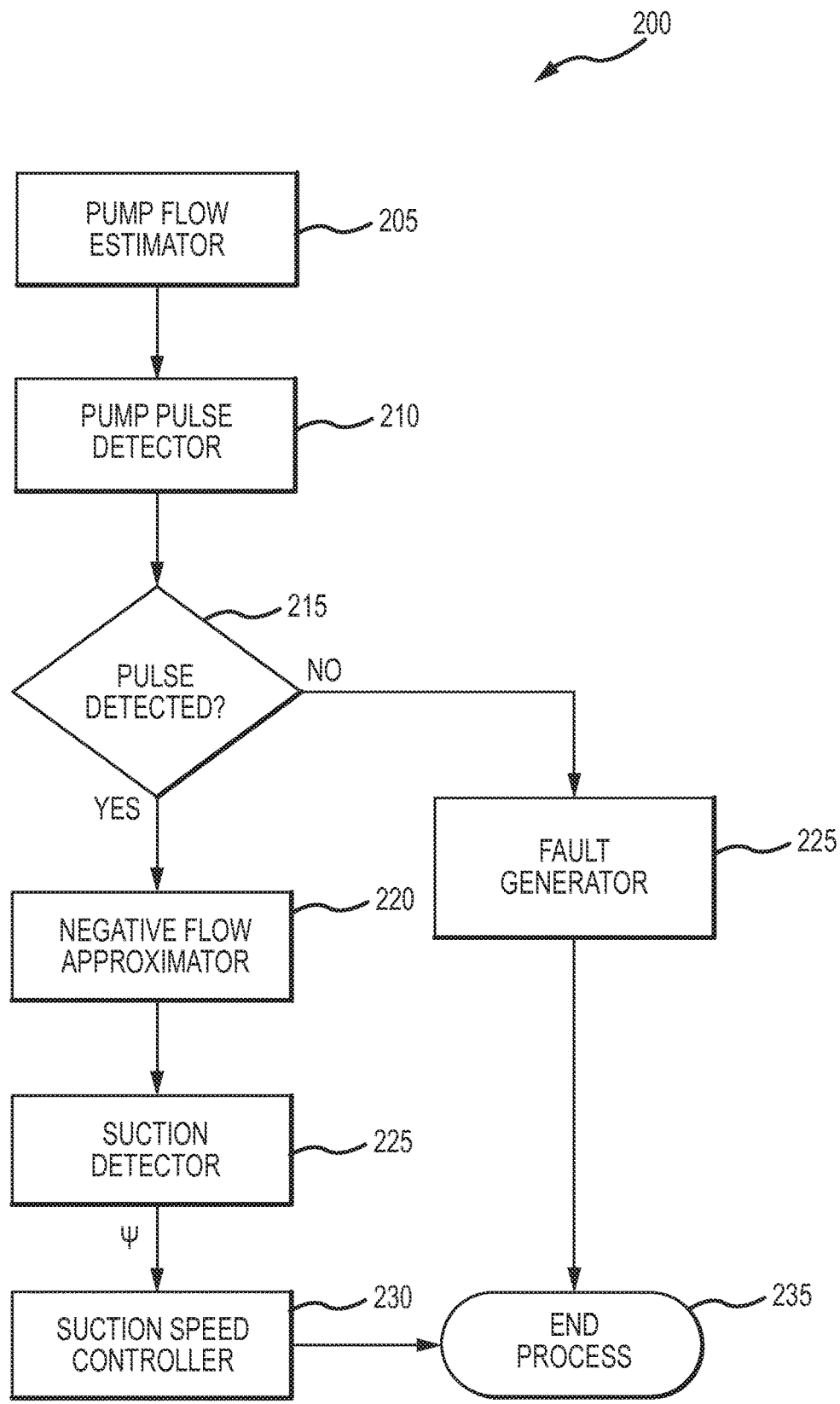
FIG. 2A is a flow diagram illustrating a method for detecting and mitigating a suction event.
Figure 2B:
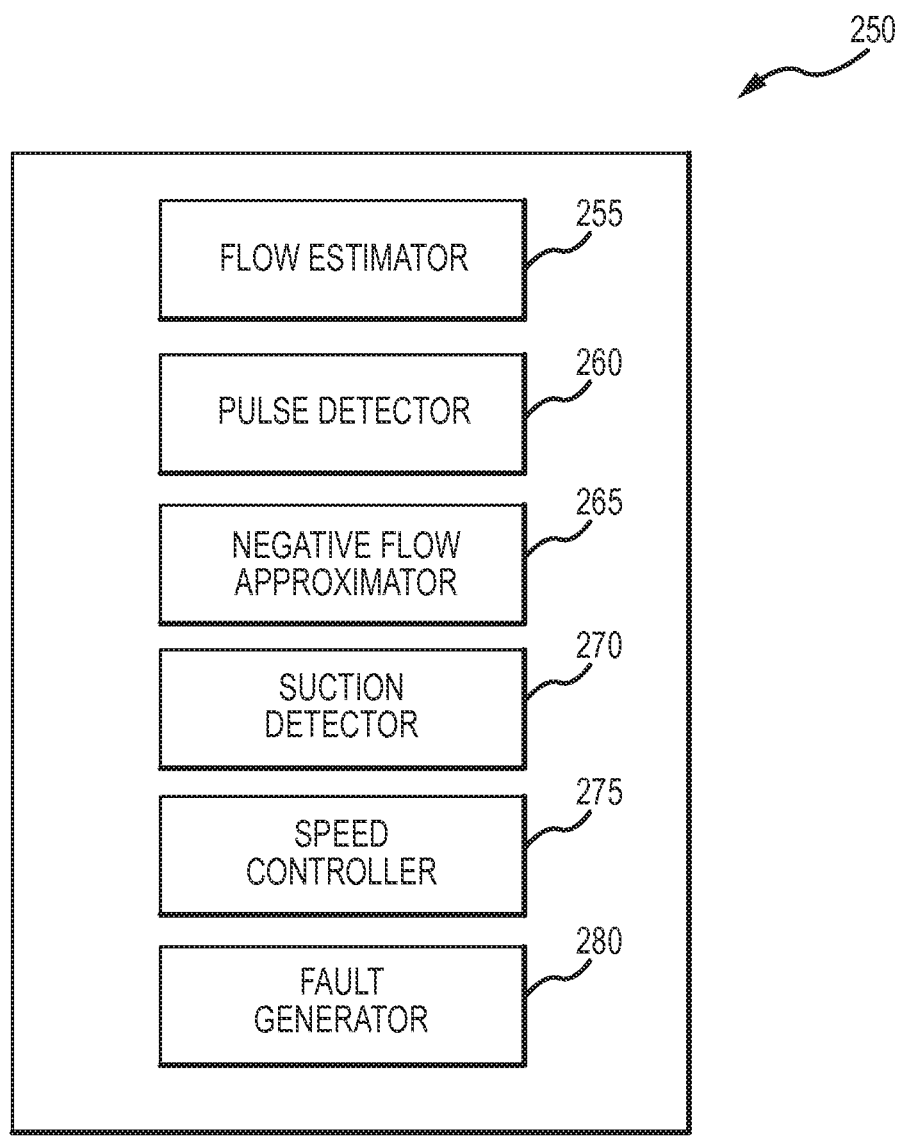
FIG. 2B is a block diagram of the components of an exemplary system for implementing the method of FIG. 2A.

FIG. 2A illustrates the flow of a method 200 in accordance with embodiments of the invention. FIG. 2B illustrates the components of an exemplary physiological control system 250 implementing the suction detection technique in accordance with the inventions. It is contemplated that the components shown in FIG. 2B may be implemented by at least one computing system or device in or as software, firmware, or hardware, and/or any combination thereof. An example of such a computing system or device is shown and described in connection with FIG. 11 below. Example functions for suction detection and mitigation using the illustrated system will now be described with respect to an exemplary left ventricular assist device (LVAD).

Referring FIGS. 2A and 2B, in step 205 the pump flow estimator component 255 takes various pump and system parameters like pump speed, pump current, pump voltage, pump power transfer characteristics and other system or vital-related parameters like Hematocrit to provide the estimated flow output. The pump characteristics can be used to determine flow in various ways. In one embodiment, pump power and speed inputs are used to determine the estimated flow. Other methods suitable for obtaining the flow waveform are acceptable as long as the methods can provide real-time flow estimation within the pump requirements, e.g., at 100 Hz and with a tolerance of +/−0.5 LPM, including a direct flow measurement.

Figure 3:
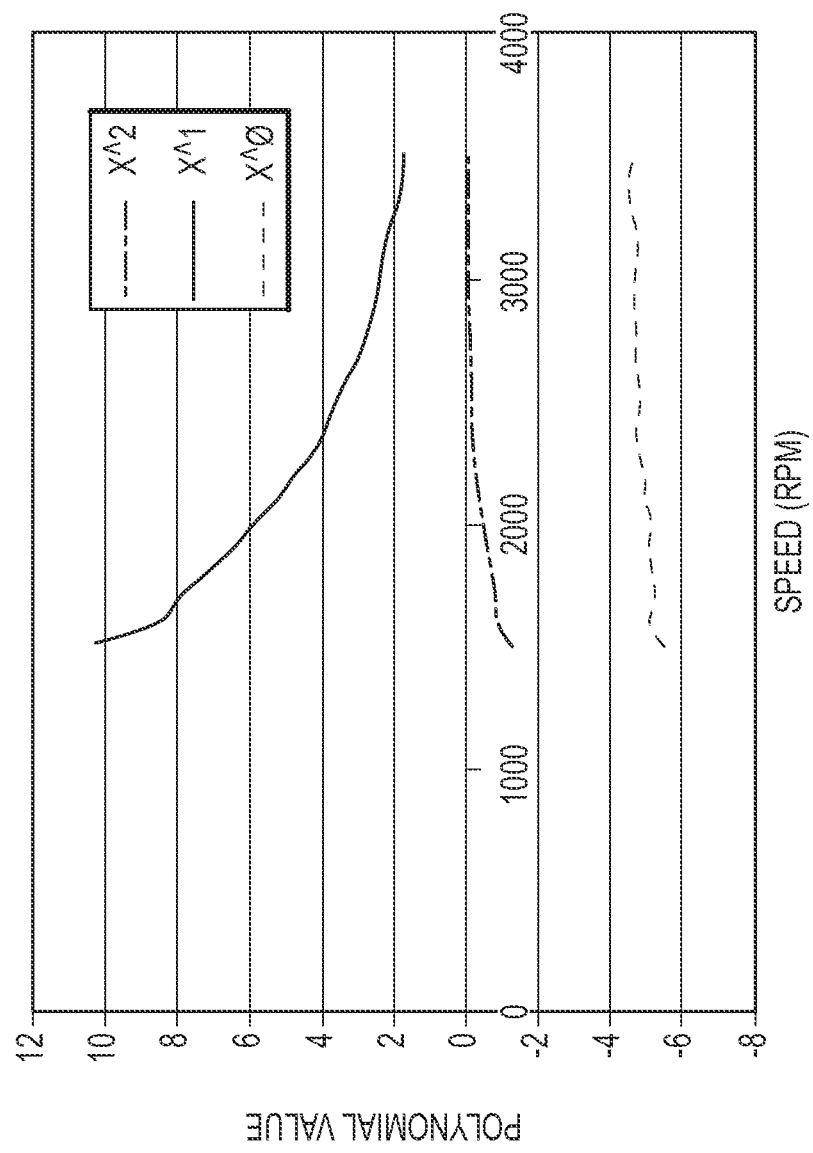
FIG. 3 is a chart showing the coefficients of the quadratic equation for the current pump speed used for flow estimation.
Figure 4:
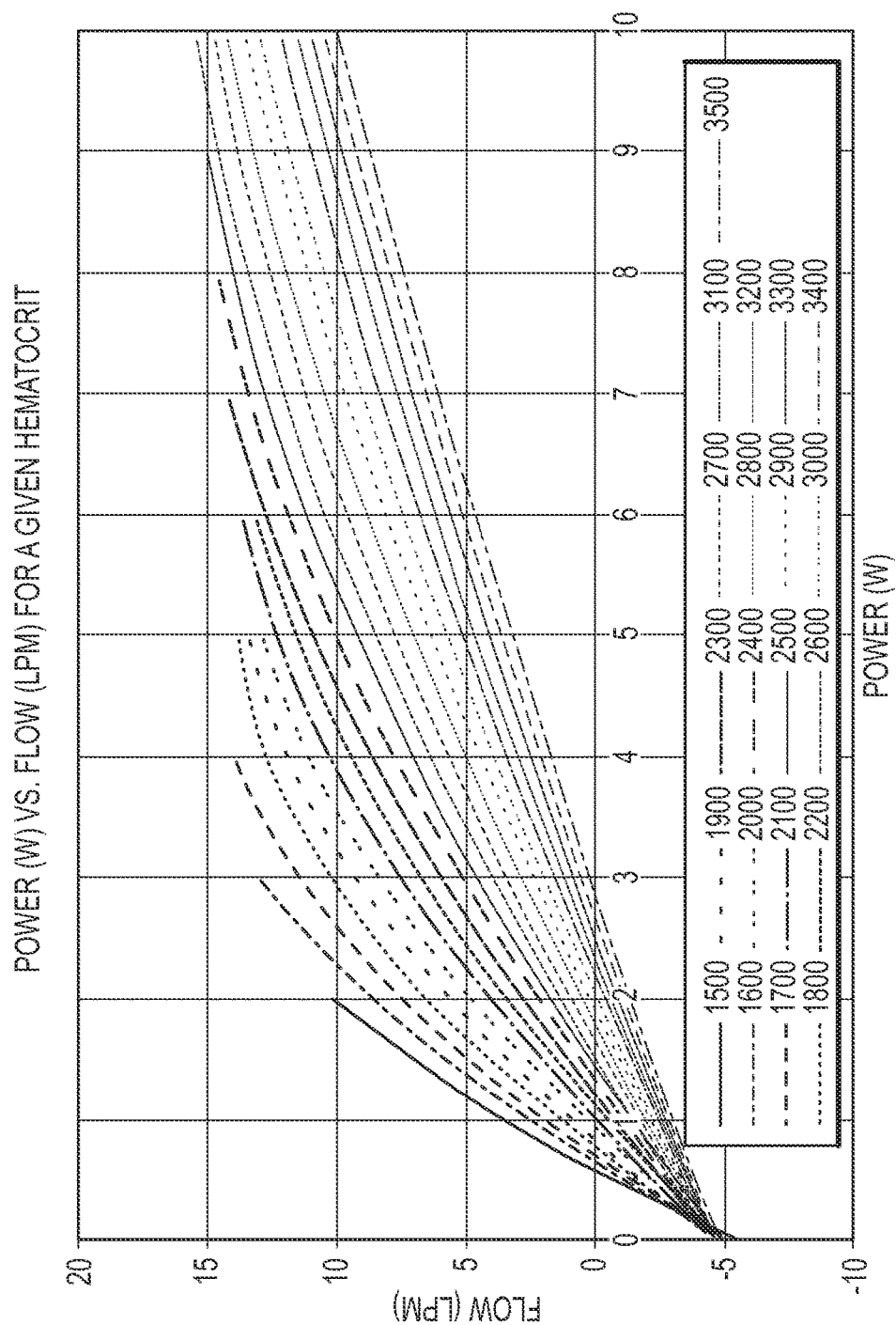
FIG. 4 is a chart showing the power to flow transform for various pump speed values for a given hematocrit.

The method described herein differs from conventional techniques in several respects. In one aspect, instead of interpolating the data sets defining the power to flow transform, the coefficients of the quadratic equation for the current pump speed as shown in the chart in FIG. 3 are interpolated. In this example, the $x^1$ trend is the topmost trend, the $x^2$ trend is the middle trend, and the $x^0$ trend is the bottommost trend. From there, the chart in FIG. 4 shows the power to flow transform for various pump speed values for a given Hematocrit. In this example, the 1500 Hematocrit trend deduced by collecting power to flow transforms for various blood hematocrit values and adjusted accordingly in real-time.

Figure 5:
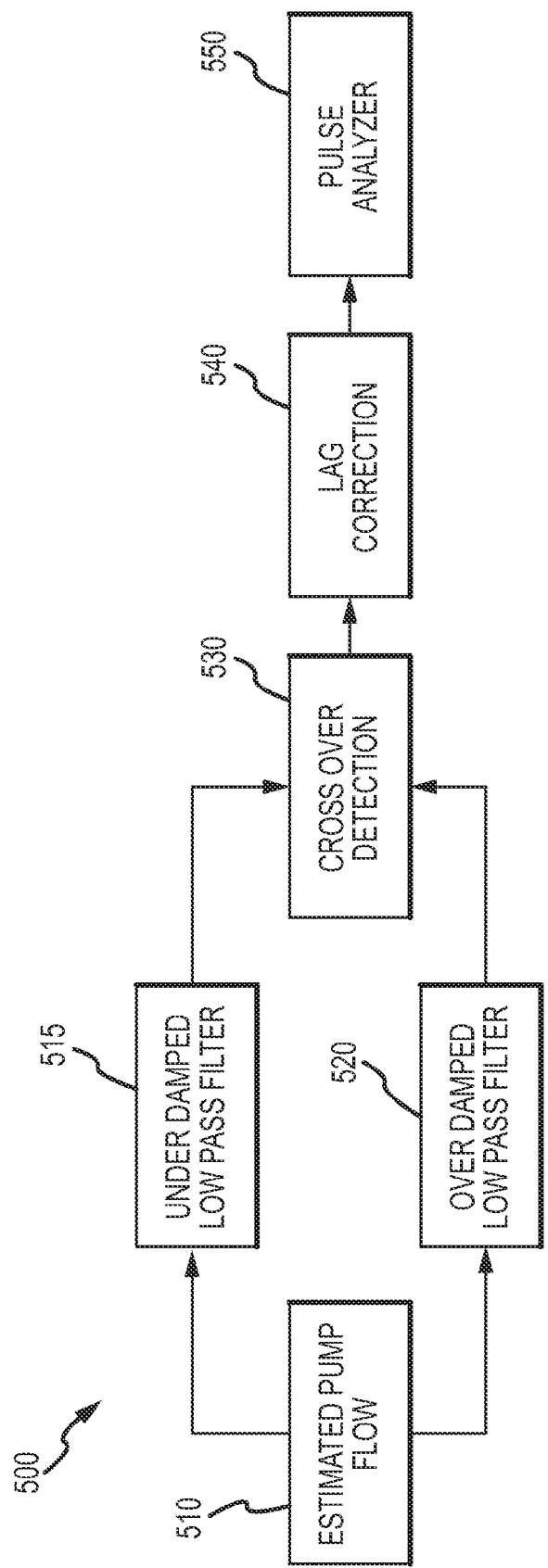
FIG. 5 is a flow diagram for the method of detecting a pump pulse in accordance with the invention.

In block 210 a pump pulse detector 260 takes the estimated flow from flow estimator 205 as an input and identifies pulses in the flow measurement to allow data analysis at individual pulse level. FIG. 5 demonstrates one possible method 500 of detecting pulses. At block 510, pump flow is estimated. The estimated flow is then subjected to an under damped low pass filter (block 515), and an over damped low pass filter (block 520). The over damped and under damped signals are superimposed on each other and cross over points are detected at block 530. Lag correction is conducted at block 540, and the resulting pulse is then analyzed at block 550. FIG. 7 The cross over points identified at the first rising edge is depicted as RCO1 shows the start of the pulse and at the second rising edge is depicted as RCO2 shows the end of the pulse. The cross over point identified at the falling edge of the pulse as FCO and shows the end of systole and the beginning of the diastole.

Pulse detector 260 monitors the pulse detector output and validates if the output pulse satisfies the acceptance criteria to ensure that a valid pulse is passed along. The acceptance criteria may include, but is not limited to, peak-to-peak flow, minimum flow, minimum and maximum pulse frequency or period, etc. If the pulse validation is successful, it passes it on to a negative flow estimator 265 at block 220. Otherwise, it transfers control to the fault generator 280 at block 225. The exemplary physiological control application called for a minimum peak-to-peak pulse of at least 1 LPM, a mean flow of at least 1 LPM, a minimum pulse period of 333 msec (~180 beats/min), and a maximum pulse period of 1.5 sec (~40 beats/min). If the pulse does not meet these criteria, it will raise fault at block 225.

If a pulse is detected in block 215, then control is turned to a negative flow approximator 265 in step 220. Negative flow approximation is generally necessary to overcome the limitation of using the pump as a flow sensor. Additionally, conventional pump systems do not have a way to measure negative flows. Negative flow approximator 265 takes the individual pulse from the pulse detector 260 as an input and tests it to see if it needs negative flow correction. In cases where the correction is needed, approximator 265 adjusts the signal and passes it on to the next component in the process.

Block 220 provides an approximation which may or may not reflect the true measurement. Accordingly, FIG. 6A and FIG. 6B show a type of pulse and the correction which may be made to approximate the negative flow. In FIG. 6A negative flow approximation is based on an extended negative pulse where the diastolic phase of the pulse shows minimal noise. In FIG. 6B negative flow approximation is based on an inverted negative pulse where the diastolic phase of the pulse shows detectable noise.

In block 225, a suction detector 270 evaluates the pulse characteristic from negative flow approximator 265 and provides a quantifiable measure for the existence of the suction condition using the method described below. For the exemplary application, $\Psi > 75\%$ is used as a determining factor for the declaration of the presence of suction.

In block 230, the value from the Suction Detector 270 is passed on to a suction speed controller 275 to make appropriate adjustments to the speed according the pulse suction index $\Psi$ output.

The index PSI/SI/$\Psi$ is calculated by identifying a suction marker which is located in the diastolic phase of the pump flow pulse as shown in FIG. 7.

With reference to FIGS. 2A and 7, the suction marker is located using the midpoint in the diastolic phase as a reference point approaching towards the minima of the diastolic segment of the pump flow pulse such that a minimum suction marker flow (SMF) threshold $SMF_{Min}$ is reached. The point identified on the pump flow curve where the $SMF_{Min}$ is reached is defined as the Suction Marker Location (SML).

SML is used to identify the primary suction probability of the suction for given pulse using the formula given below.

$$SP = 1 - \frac{SP_{R1}}{SP_{R2}}$$

Where,
SP=Suction Probability.
$SP_{R1}$=Suction Probability Reference 1 is the time between SML and FCO.
$SP_{R2}$=Suction Probability Reference 2 is the pump pulse time period.
FIG. 8 elaborates on these terms graphically.
Using the Suction Probability SP, Pump Pulse Suction Index PSI or Suction Index SI or '$\Psi$' is derived as follows.

$$\Psi = 100 \times SP\left(1 - \frac{PA_{R1}}{PA_{R2}}\right)$$

Where,
$\Psi$=Suction Index, %
SP=Suction Probability.
$PA_{R1}$=Pulse Area Reference 1 is the area defined by the pulse region overlapping the area $PA_{R2}$.
$PA_{R2}$=Pulse Area Reference 2 is the right triangular area defined time period between $RCO_2$ and SML and the difference of flow magnitude at $RCO_2$ and MNL.
FIG. 9 elaborates on the above terms graphically.

With continued reference to FIGS. 2A and 2B, in block 230 suction speed controller 275 takes the suction index $\Psi$ and low pump speed limit as inputs, and based on current pump speed and historical presence of suction condition, makes adjustments to the pump speed necessary to mitigate a suction condition or to recover the clinician specified patient speed while minimizing the introduction of suction events over time as the speed is restored to its set-point. For both speed reduction and speed increase a binary search strategy may be used for its fast convergence to the optimal speed set-point along with a maximum upper bound for the speed set-point step change. Controller 275 can also keep track of the trends of Estimated Pump Flow, Diastolic Averages, Pulsatility Index, Flow Waveform Magnitude Asymmetry and Pulse Magnitude. The controller 275 may also validate the presence of suction and detection of conditions like inflow/outflow obstruction.

While this type of control provides a means of suction mitigation, in some clinical settings and for some patient physiologies a means to disable the control of speed will be required. For those scenarios a provision to enable/disable Suction Speed Control may be desirable as a user configurable item. The default value may be enabled, and the feature can be disabled by the clinician as needed.

In block 225, a fault generator 280 is intended to provide visual/audible notifications to the patient when an invalid or no pulse is detected. The fault generator 280 may also provide a notification when a suction condition is detected that needs mitigation. These conditions may include low/no mean flow, low peak-to-peak flow, pulse rate too high or too low, suction detected, unmitigated suction and inflow/outflow obstruction conditions. The determination and selection of faults to the patient is a risk management activity. The criteria for notification to the patient may be pre-selected by a risk management team.

In block 235, the physiological control process ends.

The methods and systems described herein for suction detection and mitigation provides several advantages over existing techniques. The invention reduces the probability of false positives for suction detection. The invention provides a bounded unit less quantity for the probability of the presence of suction condition without the complications of conventional techniques. The inventive technique reduces or eliminates the need for processing intensive signal analysis, pulse recognition based on correlation and harmonic analysis schemes, or pulse recognition based on a database of known suction waveforms and matching of those waveforms against the input pump flow/power/current signal. The inventive system described above analyzes the features of the pulse so that even the detection of intermittent conditions is possible. It detects the features of the pulses and amplifies the areas and looks for features which are more pronounced in the presence of a suction event and at the same time can filter out the segments of the signal which are not relevant and are non-contributors of determining suction events. It also processes the signal at each pulse level to allow the ability to detect intermittent suction which allows detection of an onset of suction event compared to existing approaches where multiple pulses are used for the suction event detection and are unable to detect events which are intermittent. As described herein, the mitigation in response to the presence of a suction condition is optimized for its response time and minimizes the need for clinician involvement compared to existing approaches. It also minimizes the number of necessary patient visits in cases where there is a recovery from patient's physiological conditions causing suction condition over time.

One of skill in the art will appreciate from the description herein that the methods and systems may be altered and modified in accordance with the invention. Other embodiments and configurations may include a flow measurement sensor implanted with the pump which allows precision flow measurement but introduces need of additional sensing capabilities and reduces system reliability. Such a method eliminates the need for negative flow correction but the signal would still need to be analyzed for suction events using a signal matching technique using correlation and others, which require extensive signal processing thereby needing a powerful signal processor not available in pump control systems due to over-heating and power consumption issues.

Figure 10:
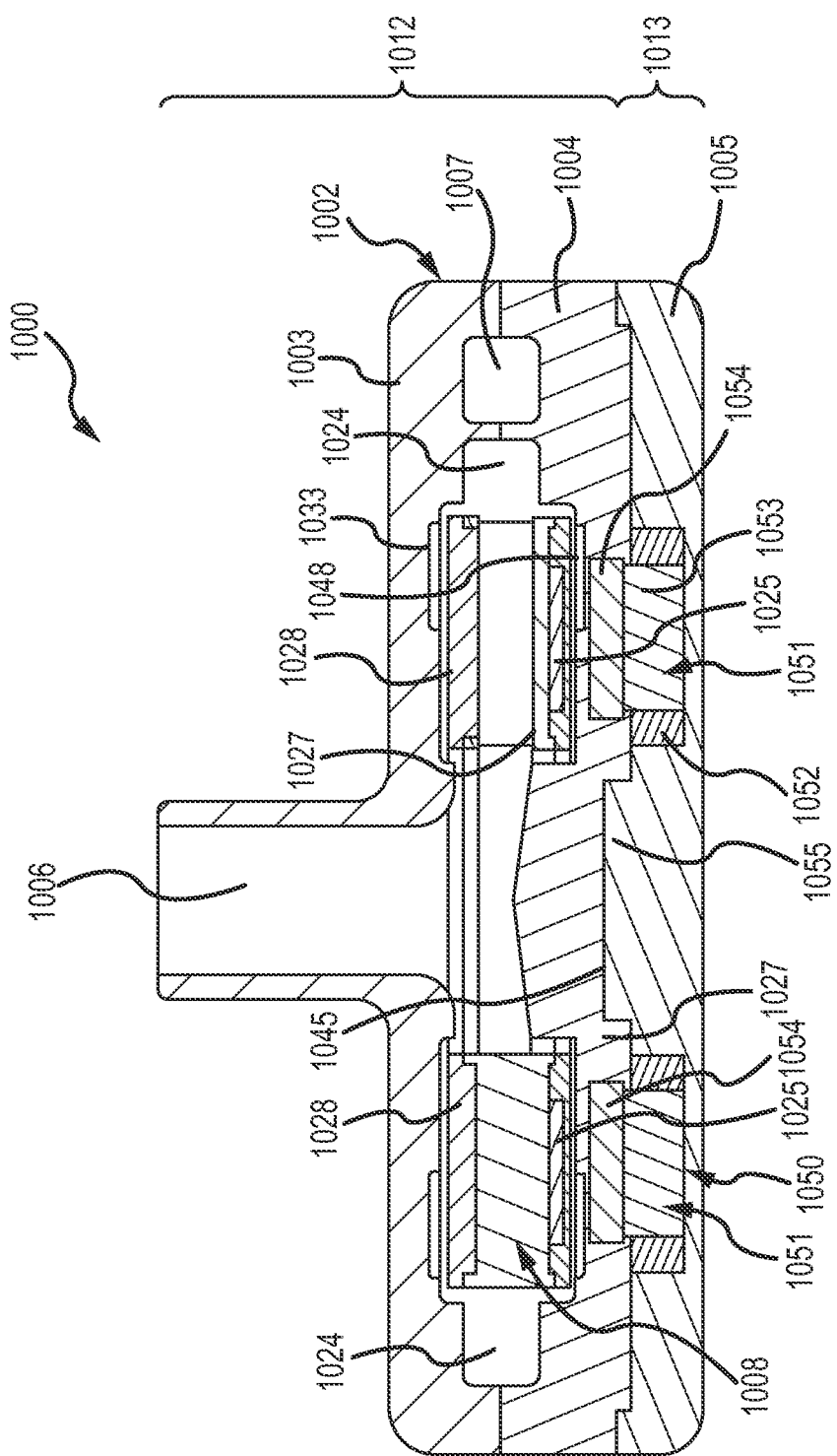
FIG. 10 is a schematic of a blood pump in accordance with the invention.

FIG. 10 shows a schematic of a blood pump 1000 in accordance with some embodiments of the invention. The techniques of the invention may be used in connection with a blood pump of this type, among others. As such, it will be appreciated that the invention is not intended to be limited to a specific embodiment of a blood pump but may be used with a wide variety of such pumps. Blood pump 1000 includes a housing 1002 having a blood inlet port 1006 and a blood outlet port (not shown) via conduit 1007; a pump unit 1012 including an impeller 1008 which has a plurality of magnetic materials (magnetic material bodies or pieces) 1025 and which rotates within the housing to feed blood; and an impeller rotational torque generation section 1013 for rotating the impeller. Housing 1002 includes a plurality of magnetic members 1054 embedded between the impeller 1008 and the impeller rotational torque generation section 1013 for transmitting a magnetically attractive force generated by the impeller rotational torque generation section 1013 to the magnetic material bodies 1025 of the impeller. The magnetic material bodies 1054 are embedded in the housing 1002 (second housing member 1004) so that the magnetic material bodies 1054 are positioned in respective recesses in the housing 1002 (second housing member 1004) and so that the magnetic material bodies 1054 form a part of the housing 1002 or second housing member 1004 (e.g., the material forming the second housing member 1004 contacts and surrounds at least a portion of the magnetic material bodies 1054 as shown in FIG. 10). The blood pump 1000 includes a non-contact bearing mechanism for rotating the impeller without contacting within the housing when the impeller is rotated by the impeller rotational torque generation section 1013.

The blood pump apparatus 1000 in the present embodiment includes the housing 1002, the pump unit 1012 composed of the impeller 1008 accommodated in the housing 1002, and the impeller rotational torque generation section 1013 for rotating the impeller. In addition, in the blood pump apparatus 1000 in the present embodiment, the impeller rotational torque generation section 1013 is attachable to and detachable from the pump unit 1012. With the impeller rotational torque generation section 1013 thus attachable to and detachable from the pump unit 1012, the impeller rotational torque generation section 1013 having no blood contact part during use can be reused, so that only the pump unit 1012 which has a blood circulating part is disposable.

The housing 1002 includes: a first housing member 1003 having the blood inlet port 1006 and a recess for accommodating an upper portion of the impeller 1008; and a second housing member 1004 having the blood outlet port and a recess for accommodating a lower portion of the impeller 1008. The housing 1002 is formed by combining the first housing member 1003 and the second housing member 1004 with each other. The interior of the housing 1002 is provided with or forms a blood chamber 1024 through which the blood inlet port 1006 and the blood outlet port communicate with each other. The blood inlet port 1006 projects substantially perpendicularly from around the center of the upper surface of the housing 1002 (the first housing member 1003). The blood inlet port 1006 is not limited to the straight pipe as illustrated, but may be a curved pipe or a bent pipe. The blood outlet port projects in a tangential direction from the side surface of the housing 1002, which is formed in a substantially hollow cylindrical shape. According to this disclosed embodiment, the blood outflow passage is of a double volute structure divided into two parts in the, but it may be of a single volute structure or of a voluteless structure.

The housing 1002 includes the plurality of magnetic members 1054 embedded between the impeller 1008 and the impeller rotational torque generation section 1013 for transmitting a magnetically attractive force generated by the impeller rotational torque generation section 1013 to the magnetic material bodies 1025 of the impeller. Specifically, the plurality of magnetic members 1054 are embedded in the second housing member 1004 (more specifically, in the bottom wall of the second housing member 1004). It is particularly preferable that the magnetic members 1054 are so embedded as not to be exposed to the inside of the blood chamber 1024, as in the pump apparatus 1 according to the present embodiment. As the magnetic member 1054, a ferromagnetic material is used.

The housing 1002, specifically the first housing member 1003 and the second housing member 1004, are formed of synthetic resin or metal. In addition, the first housing member 1003 and the second housing member 1004 have peripheral parts which make surface contact with each other, as shown in FIG. 10.

The impeller 1008 is contained in the housing 1002. Specifically, as shown in FIG. 10, a disk-shaped impeller 1008 provided with a centrally located through-hole is contained in the blood chamber 1024 formed inside the housing 1002.

As shown in FIG. 10, the impeller 1008 includes an annular member (lower shroud) 1027 forming a lower surface, an annular member (upper shroud) 1028 provided with an opening in its center and forming an upper surface, and a plurality of (for example, seven) vanes between the two members or shrouds. Between the lower shroud and the upper shroud, there are formed a plurality of (for example, seven) blood flow channels, each partitioned by the adjacent vanes. The blood flow channels communicate with the central opening of the impeller 1008, and extend to the outer peripheral edge while gradually increasing in width, starting from the central opening of the impeller 1008. In other words, the vanes are each formed between the adjacent blood flow channels. In the present embodiment, the blood flow channels and the vanes are provided at regular angular intervals and in substantially the same shape, respectively.

As shown in FIG. 10, the impeller 8 has a plurality of (for example, six) magnetic material bodies or pieces 1025 (permanent magnets; driven magnets) embedded therein. In the present embodiment, the magnetic material bodies 1025 are embedded in the lower shroud 1027. The magnetic material bodies 1025 (permanent magnets) thus embedded are attracted toward the impeller rotational torque generation section 1013 side by stators 1051 of the impeller rotational torque generation section 1013 and, also, receive a rotation torque of the impeller rotational torque generation section 1013 through the magnetic members embedded in the housing 1002 (the second housing member 1004).

In addition, where a certain number of magnetic bodies 1025 are embedded as in the present embodiment, magnetic coupling with the plurality of stators 1051 can be secured sufficiently. Preferred shapes of the magnetic material bodies 1025 (permanent magnet) include a circle, a sector and, further, a ring (an integral form in which N poles and S poles are alternately polarized). The impeller members are formed of a highly corrosion-resistant metal (titanium, stainless steel SUS316L, or the like) or synthetic resin. As the synthetic resin here, those which have been described above as material for the housing can be preferably used.

The blood pump apparatus 1000 disclosed here includes a non-contact bearing mechanism for rotating the impeller without contacting the inner surface of the housing when the impeller is rotated by the impeller rotational torque generation section 1013.

In the pump apparatus 1000 disclosed here, the non-contact bearing mechanism is composed of grooves for hydrodynamic bearing 1048 provided in the inner surface of the housing 1002 on the impeller rotational torque generation section 1013 side, in other words in a surface (bottom wall surface) of the recess in the second housing member 1004. The impeller is rotated, without contact, under a dynamic pressure bearing effect offered by a dynamic pressure generated between a surface (groove for hydrodynamic bearing formed part) 1042 in which the grooves for hydrodynamic bearing are formed and the impeller 1008, by rotation thereof at a rotating speed of not less than a predetermined value. The groove for hydrodynamic bearing formed part is formed in a size corresponding to a bottom surface (a surface on the impeller rotational torque generation section side) of the impeller 1008. In the pump apparatus 1000 disclosed here, each of the grooves for hydrodynamic bearing 1048 has its one end on the peripheral edge (circumference) of a circular part slightly outwardly spaced from the center of the surface of the recess in the second housing member, and extends therefrom nearly to the outer edge of the recess surface in a vortex form (in other words, in a curved form) while gradually increasing in width. The grooves for hydrodynamic bearing 1048 are plural in number, are the same shape (inclusive of substantially the same shape), and are arranged at regular (equal) intervals (inclusive of substantially equal intervals). The grooves for hydrodynamic bearing 1048 are each a recess, the depth of which is preferably about 0.005 to 0.4 mm. The number of the grooves for hydrodynamic bearing 1048 is preferably about 6 to 36. In the present example, twelve grooves for hydrodynamic bearing are arranged at regular (equal) angular intervals about the center axis of the impeller. The grooves for hydrodynamic bearing 1048 in the pump apparatus disclosed here have a so-called inward spiral groove shape. In the process of pumping fluid by the action of the groove for hydrodynamic bearing formed part, clockwise rotation of the impeller raises the pressure from the outer diameter side toward the inner diameter side of the groove part, so that a force in the opposite direction is obtained between the impeller 1008 and the housing 1002 forming the groove for hydrodynamic bearing formed part, and this force serves as a dynamic pressure.

The impeller 1008 is attracted toward the impeller rotational torque generation section 1013 side at the time of rotation. The presence of the groove for hydrodynamic bearing formed part as above-mentioned helps ensure that, by the dynamic pressure bearing effect provided between the groove for hydrodynamic bearing formed part of the housing and the bottom surface of the impeller 1008 (or between the groove for hydrodynamic bearing formed part of the impeller and the housing inner surface), the impeller 1008 is separated from the housing inner surface, and is rotated without contact, whereby a blood flow channel is secured between the lower surface of the impeller and the housing inner surface, and blood stagnation between these surfaces and the resultant thrombus formation are prevented from occurring. Further, in a normal condition, the groove for hydrodynamic bearing formed part exhibits a stirring action between the lower surface of the impeller and the housing inner surface, so that partial blood stagnation between these surfaces is inhibited or prevented from occurring.

The groove for hydrodynamic bearing formed part may be provided in that surface of the impeller 1008 which is on the impeller rotational torque generation section side, not on the housing side. In this case, also, the same configuration as that of the groove for hydrodynamic bearing formed part described above is preferably adopted. Specifically, the grooves for hydrodynamic bearing may be provided in that surface of the impeller 1008 which is on the impeller rotational torque generation section 1013 side (in other words, in the bottom surface of the impeller 1008).

The pump apparatus 1000 in the present embodiment can be constructed so that the housing inner surface on the opposite side to the impeller rotational torque generating part side (i.e., the surface of the recess in the first housing member 1003) may also be provided with a groove for hydrodynamic bearing formed part (second groove for hydrodynamic bearing formed part) having a plurality of grooves for hydrodynamic bearing (second grooves for hydrodynamic bearing) 1033.

The impeller rotational torque generation section 1013 of the blood pump apparatus 1000 according to the present embodiment, as shown in FIG. 10, is composed of a motor stator 50 including a plurality of stators 1051 disposed on the circumference of a circle (arranged in an annular form). A third housing member 1005 is provided with an annular recess (doughnut-shaped recess), and the plurality of stators 1051 are contained in the third housing member 1005, in the state of being arranged in an annular pattern (doughnut-like pattern). The stator 1051 has a stator core 1053 and a stator coil 1052 wound around the stator core 1053. In the pump apparatus 1000 according to the present embodiment, six stators 1051 form the stator motor 1050. As the stator coil 1052, a multilayer wound stator coil is used. With the direction of current flowing in the stator coils 1052 of the respective stators 1051 switched over or alternating a rotating magnetic field is generated, by which the impeller is attracted and rotated.

In the blood pump apparatus 1000 in the present embodiment, as shown in FIG. 10, the respective magnetic members 1054 of the housing 1002 (specifically, the second housing member 1004) are so disposed as to be located on, or in overlying relation to, the stator cores 1053 of the respective stators 1051 described above. That is, each of the plurality of magnetic members 1054 is positioned in circumferential alignment with one of the stator cores 1053 of the stators 1051. The stator cores 1053 in the present embodiment are each sector-shaped a, and correspondingly, the magnetic members 1054 are also each sector-shaped. The magnetic members 1054 are slightly greater in size than the stator cores 1053.

Further, in the blood pump apparatus 1000 according to the present embodiment, as shown in FIG. 10, each of the magnetic members 1054 of the housing 1002 (specifically, the second housing member 1004) makes direct contact with the stator core 1053 of each of the stators 1051. More specifically, in this pump apparatus 1000, an upper end portion of the stator core 1053 projects upwardly slightly beyond the stator coil 1052, and the projecting portion is exposed. The magnetic member 1054 is so embedded in the second housing member 1004 that its lower surface is exposed; further, the portion where the lower surface of the magnetic member 1054 is exposed forms a recess in which the projecting portion of the stator core 1053 is accommodated. Therefore, the magnetic member 1054 and the stator core 1053 are in contact with each other. This helps ensure that a magnetic force generated in the stator 1051 can be securely transmitted to the magnetic member 1054.

In the pump apparatus 1000 according to the present embodiment, the pump unit 1012 and the impeller rotational torque generation section 1013 can be attached to and detached from each other, and both of them have a connecting mechanism. In the pump apparatus 1000 in the present embodiment, the second housing member of the pump unit 1012 is provided at its bottom surface with a first engaging part (a recess) 1045, whereas the housing 1005 of the impeller rotational torque generation section 1013 is provided with a second engaging part (specifically, a projection) 1055 which engages the first engaging part (recess) 1045. The engagement between the first engaging part (recess) 1045 of the pump unit 1012 and the second engaging part (projection) 1055 of the impeller rotational torque generation section 1013 connects the units to each other.

Figure 11:
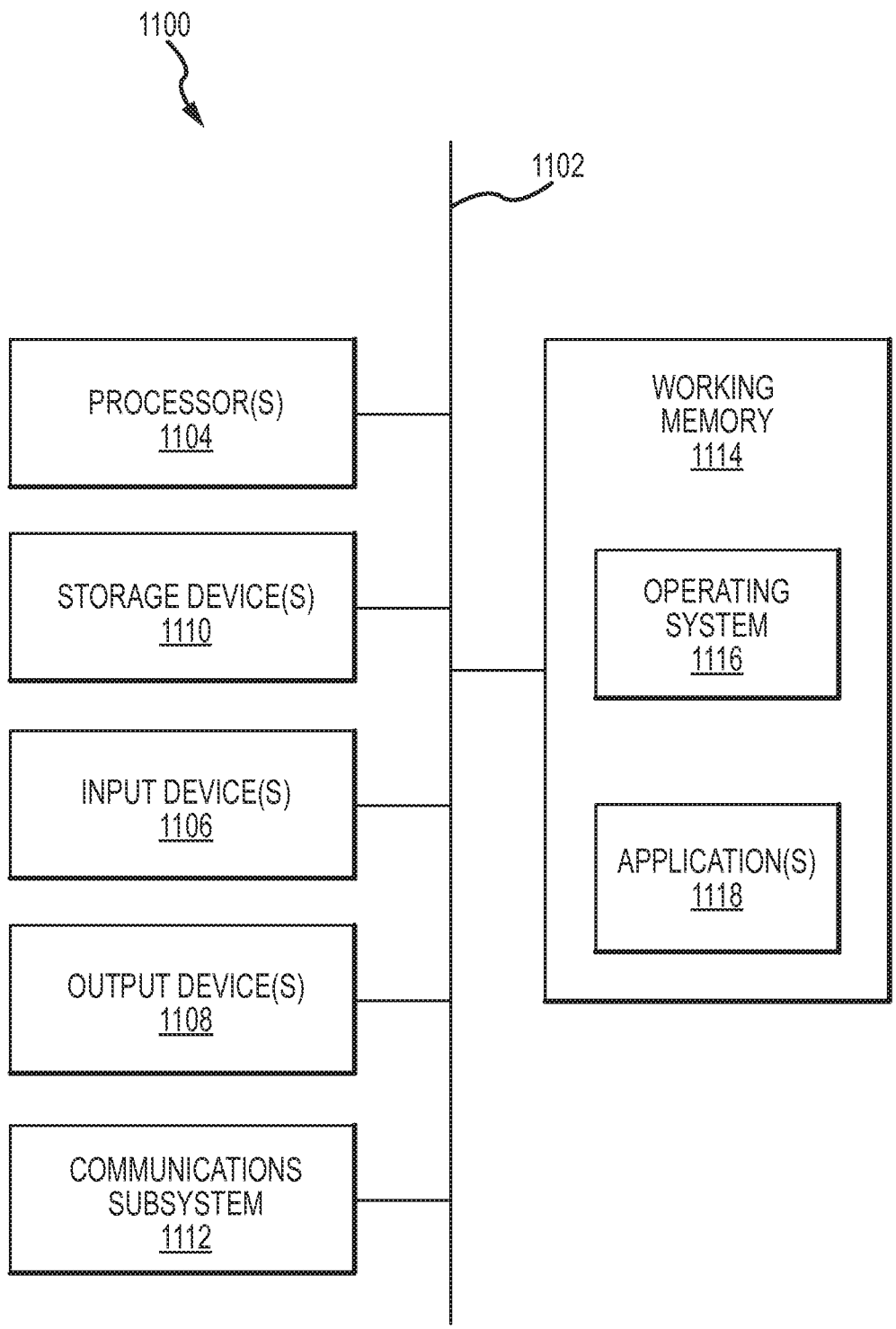
FIG. 11 shows an example computing system or device.

FIG. 11 shows an example computer system or device 1100 in accordance with the disclosure. An example of a computer system or device includes a medical device, a desktop computer, a laptop computer, a tablet computer, and/or any other type of machine configured and/or arranged for performing calculations.

The example computer device 1100 may be configured and/or arranged to perform and/or include instructions that, when executed, cause the computer system 1100 to perform a method for or of detecting a suction event of a blood pump such as that discussed in the context of the present disclosure. For example, the example computer device 1100 may be configured to perform and/or include instructions that, when executed, cause the computer system 1100 to perform at least one of the following steps: determining a flow waveform of the pump; identifying pulses in the flow waveform; determining a negative flow pulse based on a valid identification of a pulse; and evaluating a characteristic of the pulse for an existence of a suction condition.

Additionally, or alternatively, the example computer device 1100 may be configured and/or arranged to perform and/or include instructions that, when executed, cause the computer system 1100 to estimate the flow waveform by solving for the following quadratic equation:

$$F = Ap^2 + Bp + C$$

Where,
F=Flow Rate (LPM)
p=Pump Power (W) adjusted for hematocrit (This could also be based on current)
A=Interpolated X2 Polynomial coefficient for the given pump speed.
B=Interpolated X1 Polynomial coefficient for the given pump speed.
C=Interpolated X0 Polynomial coefficient for the given pump speed.

Additionally, or alternatively, the example computer device 1100 may be configured and/or arranged to perform and/or include instructions that, when executed, cause the computer system 1100 to select a pulse segmentation from the group consisting of: The Pulse Average, The Pulse Minima (Turf), The Pulse Maxima (Crest), The pulse falling cross-over point, The Systolic Average (SSA), The Diastolic Average (DSA), The Systolic Pulse Index (SPI), The Diastolic Pulse Index (DPI), The Pulse Flow Index (PFI), The Negative Flow Correction, The Pulse Asymmetry Index, The Pulse Suction Index ($\Psi$), The Pulse Duty Cycle (PDC), The Pulse Frequency (PHZ), and a combination of the same.

Additionally, or alternatively, the example computer device 1100 may be configured and/or arranged to perform and/or include instructions that, when executed, cause the computer system 1100 to implement a method of or for negative flow approximation, wherein the diastolic segment of the pump flow pulse is used to determine the type of approximation and correction to determined flow is made based on the type of approximation identified.

Additionally, or alternatively, the example computer device 1100 may be configured and/or arranged to perform and/or include instructions that, when executed, cause the computer system 1100 to determine a quantity of the suction condition, and wherein the quantity is named after the Greek Symbol ($\Psi$) pronounced as PSI and used as an acronym with the definition of Pulse Suction Index (PSI).

Additionally, or alternatively, the example computer device 1100 may be configured and/or arranged to perform and/or include instructions that, when executed, cause the computer system 1100 to implement a method of or for a method of calculating a pulse suction index ($\Psi$) according to the formula:

$$\Psi = 100 \times SP\left(1 - \frac{PA_{R1}}{PA_{R2}}\right)$$

Where,
$\Psi$=Suction Index, %
SP=Suction Probability
$PA_{R1}$=Pulse Area Reference 1 is the area defined by the pulse region overlapping the area $PA_{R2}$
$PA_{R2}$=Pulse Area Reference 2 is the right triangular area defined time period between
$RCO_2$ and SML and the difference of flow magnitude at $RCO_2$ and MNL Additionally, or alternatively, the example computer device 1100 may be configured to perform and/or include instructions that, when executed, cause the computer system 1100 to use a binary search to increase or decrease the pump speed when suction criteria is met, and the step change of the pump speed of the binary search is bounded by an upper limit identified as safe for the patient population.

Additionally, or alternatively, the example computer device 1100 may be configured to perform and/or include instructions that, when executed, cause the computer system 1100 to derive an indication wherein an increase in MIN (DSA) with the an increase in MIN(DSA) with the decrease in speed may additionally indicate recovery from suction condition.

Additionally, or alternatively, the example computer device 1100 may be configured and/or arranged to perform and/or include instructions that, when executed, cause the computer system 1100 to derive an indication wherein a decrease in MEAN(PAI) with the decrease in speed may additionally indicate recovery from suction condition.

Additionally, alternatively, the example computer device 1100 may be configured and/or arranged to perform and/or include instructions that, when executed, cause the computer system 1100 to derive an indication wherein a decrease in MEAN(DPI) with the decrease in speed may additionally indicate recovery from suction condition.

Additionally, alternatively, the example computer device 1100 may be configured and/or arranged to perform and/or include instructions that, when executed, cause the computer system 1100 to derive an indication wherein a decrease in PSI($\Psi$) with the decrease in speed will most likely indicate recovery from suction condition.

Additionally, alternatively, the example computer device 1100 may be configured and/or arranged to perform and/or include instructions that, when executed, cause the computer system 1100 to determine or identify or detect that a lowest allowable pump speed for recovery from suction condition is based on a Low Speed Limit. In some examples, the Low Speed Limit is based on an input from a clinician as detected by the device 1100.

Additionally, alternatively, the example computer device 1100 may be configured and/or arranged to perform and/or include instructions that, when executed, cause the computer system 1100 to implement the step of evaluating by: locating a suction marker reference point based on a midpoint in the diastolic phase; identifying a suction marker location where a suction marker flow minimum is reached; and using the suction marker location to identify a probability of a suction condition.

Additionally, alternatively, the example computer device 1100 may be configured and/or arranged to perform and/or include instructions that, when executed, cause the computer system 1100 to implement a step of decreasing a speed of the pump in response to identification of the existence of a suction condition.

The computer device 1100 is shown comprising hardware elements that may be electrically coupled via a bus 1102 (or may otherwise be in communication, as appropriate). The hardware elements may include a processing unit with one or more processors 1104, including without limitation one or more general-purpose processors and/or one or more special-purpose processors (such as digital signal processing chips, graphics acceleration processors, and/or the like); one or more input devices 1106, which may include without limitation a remote control, a mouse, a keyboard, and/or the like; and one or more output devices 1108, which may include without limitation a presentation device (e.g., television), a printer, and/or the like.

The computer system 1100 may further include (and/or be in communication with) one or more non-transitory storage devices 1110, which may comprise, without limitation, local and/or network accessible storage, and/or may include, without limitation, a disk drive, a drive array, an optical storage device, a solid-state storage device, such as a random access memory, and/or a read-only memory, which may be programmable, flash-updateable, and/or the like. Such storage devices may be configured to implement any appropriate data stores, including without limitation, various file systems, database structures, and/or the like.

The computer device 1100 might also include a communications subsystem 1112, which may include without limitation a modem, a network card (wireless and/or wired), an infrared communication device, a wireless communication device and/or a chipset such as a Bluetooth™ device, 1102.11 device, WiFi device, WiMax device, cellular communication facilities such as GSM (Global System for Mobile Communications), W-CDMA (Wideband Code Division Multiple Access), LTE (Long Term Evolution), etc., and/or the like. The communications subsystem 1112 may permit data to be exchanged with a network (such as the network described below, to name one example), other computer systems, and/or any other devices described herein. In many embodiments, the computer system 1100 will further comprise a working memory 1114, which may include a random access memory and/or a read-only memory device, as described above.

The computer device 1100 also may comprise software elements, shown as being currently located within the working memory 1114, including an operating system 1116, device drivers, executable libraries, and/or other code, such as one or more application programs 1118, which may comprise computer programs provided by various embodiments, and/or may be designed to implement methods, and/or configure systems, provided by other embodiments, as described herein. By way of example, one or more procedures described with respect to the method(s) discussed above, and/or system components might be implemented as code and/or instructions executable by a computer (and/or a processor within a computer); in an aspect, then, such code and/or instructions may be used to configure and/or adapt a general purpose computer (or other device) to perform one or more operations in accordance with the described methods.

A set of these instructions and/or code might be stored on a non-transitory computer-readable storage medium, such as the storage device(s) 1110 described above. In some cases, the storage medium might be incorporated within a computer system, such as computer system 1100. In other embodiments, the storage medium might be separate from a computer system (e.g., a removable medium, such as flash memory), and/or provided in an installation package, such that the storage medium may be used to program, configure, and/or adapt a general purpose computer with the instructions/code stored thereon. These instructions might take the form of executable code, which is executable by the computer device 1100 and/or might take the form of source and/or installable code, which, upon compilation and/or installation on the computer system 1100 (e.g., using any of a variety of generally available compilers, installation programs, compression/decompression utilities, etc.), then takes the form of executable code.

It will be apparent that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer device 1100) to perform methods in accordance with various embodiments of the disclosure. According to a set of embodiments, some or all of the procedures of such methods are performed by the computer system 1100 in response to processor 1104 executing one or more sequences of one or more instructions (which might be incorporated into the operating system 1116 and/or other code, such as an application program 1118) contained in the working memory 1114. Such instructions may be read into the working memory 1114 from another computer-readable medium, such as one or more of the storage device(s) 1110. Merely by way of example, execution of the sequences of instructions contained in the working memory 1114 may cause the processor(s) 1104 to perform one or more procedures of the methods described herein.

The terms "machine-readable medium" and "computer-readable medium," as used herein, may refer to any non-transitory medium that participates in providing data that causes a machine to operate in a specific fashion. In an embodiment implemented using the computer device 1100, various computer-readable media might be involved in providing instructions/code to processor(s) 1104 for execution and/or might be used to store and/or carry such instructions/code. In many implementations, a computer-readable medium is a physical and/or tangible storage medium. Such a medium may take the form of a non-volatile media or volatile media. Non-volatile media may include, for example, optical and/or magnetic disks, such as the storage device(s) 1110. Volatile media may include, without limitation, dynamic memory, such as the working memory 1114.

Example forms of physical and/or tangible computer-readable media may include a floppy disk, a flexible disk, hard disk, magnetic tape, or any other magnetic medium, a compact disc, any other optical medium, ROM (Read Only Memory), RAM (Random Access Memory), and etc., any other memory chip or cartridge, or any other medium from which a computer may read instructions and/or code. Various forms of computer-readable media may be involved in carrying one or more sequences of one or more instructions to the processor(s) 1104 for execution. By way of example, the instructions may initially be carried on a magnetic disk and/or optical disc of a remote computer. A remote computer might load the instructions into its dynamic memory and send the instructions as signals over a transmission medium to be received and/or executed by the computer system 1100.

The communications subsystem 1112 (and/or components thereof) generally will receive signals, and the bus 1102 then might carry the signals (and/or the data, instructions, etc. carried by the signals) to the working memory 1114, from which the processor(s) 1104 retrieves and executes the instructions. The instructions received by the working memory 1114 may optionally be stored on a non-transitory storage device 1110 either before or after execution by the processor(s) 1104.

It should further be understood that the components of computer device 1100 can be distributed across a network. For example, some processing may be performed in one location using a first processor while other processing may be performed by another processor remote from the first processor. Other components of computer system 1100 may be similarly distributed. As such, computer device 1100 may be interpreted as a distributed computing system that performs processing in multiple locations. In some instances, computer system 1100 may be interpreted as a single computing device, such as a distinct laptop, desktop computer, or the like, depending on the context.

The invention has now been described in detail for the purposes of clarity and understanding. However, it will be appreciated that certain changes and modifications may be practiced within the scope of the appended claims.

What is claimed:

1. A method of detecting a suction event of a blood pump, comprising:
   determining a flow waveform of a fluid output of the blood pump;
   identifying a pulse in the flow waveform;
   determining a negative flow pulse based on a valid identification of the pulse;
   evaluating a characteristic of the pulse for an existence of a suction condition by:
      locating a suction marker reference point in the pulse based on a midpoint in a diastolic phase of the pulse;
      identifying a suction marker location in the pulse where a suction marker flow minimum is reached; and
      using the suction marker location to identify a probability of a suction condition; and
   modifying operation of the blood pump based at least in part on the existence of the suction condition.

2. The method as in claim 1 wherein the flow is estimated by solving for the following quadratic equation:

$$F = Ap^2 + Bp + C$$

where,
   F=Flow Rate (LPM);
   p=Pump Power (W) adjusted for hematocrit;
   A=Interpolated X2 Polynomial coefficient for a given pump speed;
   B=Interpolated X1 Polynomial coefficient for the given pump speed; and
   C=Interpolated X0 Polynomial coefficient for the given pump speed.

3. The method as in claim 1, wherein identifying the pulse comprises determining pulse segmentation using a selection from a group consisting of: the Pulse Average, the Pulse Minima (Turf), the Pulse Maxima (Crest), the pulse falling cross-over point, the Systolic Average (SSA), the Diastolic Average (DSA), the Systolic Pulse Index (SPI), the Diastolic Pulse Index (DPI), the Pulse Flow Index (PFI), the Negative Flow Correction, the Pulse Asymmetry Index, the Pulse Suction Index ($\Psi$), the Pulse Duty Cycle (PDC), the Pulse Frequency (PHZ), and a combination of the same.

4. A method to determine a quantity of a suction condition in a blood pump, comprising:
   calculating a pulse suction index ($\Psi$) according to the formula:

$$\Psi = 100 \times SP\left(1 - \frac{PA_{R1}}{PA_{R2}}\right)$$

where,
   $\Psi$=Suction Index;
   SP=Suction Probability;
   $PA_{R1}$=Pulse Area Reference 1 is the area defined by a pulse region overlapping the area $PA_{R2}$;
   $PA_{R2}$=Pulse Area Reference 2 is the right triangular area defined time period between $RCO_2$ and SML and the difference of flow magnitude at $RCO_2$ and MNL;
   $RCO_2$=Second Rising Cross-Over point;
   SML=Suction marker Location;
   MNL=Lowest flow in a Diastolic region; and
   determining the quantity of the suction condition based at least in part on the pulse suction index; and
   modifying operation of the blood pump based at least in part on the quantity of the suction condition.

5. The method as in claim 4, further comprising:
   controlling pump speed of the blood pump using the ($\Psi$), wherein a binary search algorithm of possible pump speeds is used to increase or decrease the pump speed when a determined suction criteria is met, and a step change of the pump speed is bounded by an upper limit identified as safe for a given patient population.

6. The method as in claim 4, wherein an increase in MIN(DSA) with a decrease in speed designates recovery from the suction condition, where MIN(DSA)=Minimum Pulse Diastolic Average.

7. The method as in claim 4, wherein a decrease in MEAN(WAI) with a decrease in speed designates recovery from the suction condition, where MEAN(WAI)=Mean Waveform Asymmetry Index.

8. The method as in claim 4, wherein a decrease in MEAN(PAI) with a decrease in speed designates recovery from the suction condition, where MEAN(PAI)=Mean Pulse Asymmetry Index.

9. The method as in claim 4, wherein a decrease in MEAN(DPI) with a decrease in speed designates recovery from the suction condition, where MEAN(DPI)=Mean Diastolic Pulse Index.

10. The method as in claim 4, wherein a decrease in PSI($\Psi$) with a decrease in speed designates recovery from the suction condition, where PSI($\Psi$)=Pulse Suction Index.

11. The method as in claim 6, wherein a lowest allowable pump speed for recovery from the suction condition is bounded by a Low Speed Limit.

12. A system, comprising:
 a blood pump;
 a controller configured to operate the blood pump, the controller configured to:
  determine a flow waveform of a fluid output of the blood pump;
  identify a pulse in the flow waveform;
  determine a negative flow pulse based on a valid identification of the pulse;
  evaluate a characteristic of the pulse for an existence of a suction condition by:
   locating a suction marker reference point in the pulse based on a midpoint in a diastolic phase of the pulse;
   identifying a suction marker location in the pulse where a suction marker flow minimum is reached; and
   using the suction marker location to identify a probability of a suction condition; and
  provide an output based on the existence of a suction condition.

13. The system as in claim 12, wherein the controller estimates the flow by solving for the following quadratic equation:

$$F=Ap^2+Bp+C$$

where,
F=Flow Rate (LPM);
p=Pump Power (W) adjusted for hematocrit;
A=Interpolated X2 Polynomial coefficient for a given pump speed;
B=Interpolated X1 Polynomial coefficient for the given pump speed; and
C=Interpolated X0 Polynomial coefficient for the given pump speed.

14. The system as in claim 12, wherein identifying the pulse comprises determining pulse segmentation using a selection from a group consisting of: the Pulse Average, the Pulse Minima (Turf), the Pulse Maxima (Crest), the pulse falling cross-over point, the Systolic Average (SSA), the Diastolic Average (DSA), the Systolic Pulse Index (SPI), the Diastolic Pulse Index (DPI), the Pulse Flow Index (PFI), the Negative Flow Correction, the Pulse Asymmetry Index, the Pulse Suction Index ($\Psi$), the Pulse Duty Cycle (PDC), the Pulse Frequency (PHZ), and a combination of the same.

* * * * *